(12) United States Patent
Hammond et al.

(10) Patent No.: US 9,644,230 B2
(45) Date of Patent: May 9, 2017

(54) METHOD AND DEVICE FOR DETECTING BACTERIA AND DETERMINING THE CONCENTRATION THEREOF IN A LIQUID SAMPLE

(71) Applicant: IDEXX Laboratories, Inc., Westbrook, ME (US)

(72) Inventors: Jeremy Hammond, Standish, ME (US); James Russell, North Yarmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 14/525,628

(22) Filed: Oct. 28, 2014

(65) Prior Publication Data

US 2015/0118708 A1  Apr. 30, 2015

Related U.S. Application Data

(60) Provisional application No. 61/896,877, filed on Oct. 29, 2013.

(51) Int. Cl.
*C12Q 1/06* (2006.01)
*B01L 3/00* (2006.01)

(52) U.S. Cl.
CPC ............ *C12Q 1/06* (2013.01); *B01L 3/502* (2013.01); *B01L 3/502761* (2013.01); *B01L 2200/0652* (2013.01); *B01L 2300/0681* (2013.01); *B01L 2300/0851* (2013.01); *B01L 2300/0864* (2013.01); *B01L 2300/0877* (2013.01); *B01L 2400/086* (2013.01)

(58) Field of Classification Search
CPC ...................................................... C12Q 1/06
See application file for complete search history.

(56) References Cited

U.S. PATENT DOCUMENTS

| | | | |
|---|---|---|---|
| 5,329,461 A | 7/1994 | Allen et al. ................ 702/26 |
| 5,488,567 A | 1/1996 | Allen et al. ................ 702/26 |
| 5,649,032 A | 7/1997 | Burt et al. ................. 382/284 |
| 6,160,908 A | 12/2000 | Hakozaki .................. 382/154 |
| 6,313,452 B1 | 11/2001 | Paragano et al. .......... 250/201.3 |
| 6,869,570 B2 | 3/2005 | Wardlaw .................. 422/82.05 |
| 6,873,725 B2 | 3/2005 | Xu ............................ 382/154 |
| 6,917,696 B2 | 7/2005 | Soenksen .................. 382/128 |
| 6,919,960 B2 | 7/2005 | Hansen et al. ............. 356/436 |
| 7,058,233 B2 | 6/2006 | Silber ........................ 382/256 |
| 7,068,365 B2 | 6/2006 | Hansen et al. ............. 356/246 |
| 7,630,628 B2 | 12/2009 | Ogihara ..................... 396/432 |
| 7,634,128 B2 | 12/2009 | Snow et al. ................ 382/151 |
| 7,634,129 B2 | 12/2009 | Strom ........................ 382/154 |
| 7,764,821 B2 | 7/2010 | Coumans et al. ......... 382/133 |
| 7,860,302 B2 | 12/2010 | Sato et al. ................. 382/154 |
| 7,949,161 B2 | 5/2011 | Kawanabe et al. ....... 382/128 |
| 8,149,401 B2 | 4/2012 | Stevens et al. ........... 356/335 |
| 8,179,599 B2 | 5/2012 | Jansen ....................... 359/433 |
| 8,569,076 B2 | 10/2013 | Wardlaw et al. ......... 436/523 |
| 8,780,181 B2 | 7/2014 | Olesen et al. ............. 348/46 |
| 2002/0031249 A1 | 3/2002 | Komuro et al. .......... 382/149 |
| 2003/0103277 A1 | 6/2003 | Mohwinkel ............... 359/811 |
| 2005/0068614 A1 | 3/2005 | Yoneyama et al. ....... 359/368 |
| 2007/0194244 A1 | 8/2007 | Adams et al. ............. 250/389 |
| 2008/0100703 A1 | 5/2008 | Yamada ...................... 348/79 |
| 2008/0246946 A1 | 10/2008 | Hansen et al. ............. 356/36 |
| 2009/0231689 A1 | 9/2009 | Pittsyn et al. ............. 359/363 |
| 2009/0295963 A1 | 12/2009 | Bamford et al. .......... 348/302 |
| 2010/0200728 A1 | 8/2010 | Ingber ........................ 250/205 |
| 2010/0314533 A1 | 12/2010 | Stallinga et al. .......... 250/234 |
| 2011/0042582 A1 | 2/2011 | Ingber et al. ............. 250/458.1 |
| 2011/0261164 A1 | 10/2011 | Olesen et al. ............. 348/46 |
| 2012/0244519 A1 | 9/2012 | Olesen et al. ............. 435/2 |

FOREIGN PATENT DOCUMENTS

| | | | |
|---|---|---|---|
| WO | WO2008/134678 | 11/2008 | ............ G02B 21/24 |
| WO | WO2010/063293 | 6/2010 | ............ G02B 21/36 |

OTHER PUBLICATIONS

Staudt et al. Biotechnology and Bioengineering, 2004, 88(5):585-592.*
International Search Report dated Apr. 15, 2015 and the Written Opinion of the International Searching Authority dated Apr. 15, 2015, issued from Applicant's corresponding PCT Application No. PCT/US2014/062624 filed on Oct. 28, 2014, each from the World Intellectual Property Organization (WIPO) is enclosed.
Cho H., Jönsson H., Campbell K., Melice P., Williams JW, et al. (Published Oct. 30, 2007) "*Self-Organization in High-Density Bacterial Colonies: Efficient Crowd Control*", PLoS Biol 5(11): e302. doi:10.1371/journal.pbio.0050302; PLoS Biology, vol. 5, Issue 11, e302, pp. 2614-2623. Text available at: http://journals.plos.org/plosbiology/article?id=10.1371/journal.pbio.0050302. (accessed May 14, 2015).

* cited by examiner

*Primary Examiner* — Bin Shen
(74) *Attorney, Agent, or Firm* — Bodner & O'Rourke, LLP; Gerald T. Bodner; Christian P. Bodner

(57) ABSTRACT

A method for detecting bacteria and determining the concentration thereof in a liquid sample includes the steps of taking an optical section through a container holding a volume of the liquid sample at a predetermined field of view and at a predetermined focal plane depth or angle and after a period of time has elapsed to allow non-bacteria in the sample to settle to the bottom of the container. Since bacteria auto arranges in the liquid sample, forming a lattice-like grid pattern, an optical section through the volume of auto-arranged bacteria may be used to measure the quantity of bacteria residing in that section. A container for holding the liquid sample has particular structure which aids in separating the non-bacteria from the bacteria.

9 Claims, 25 Drawing Sheets

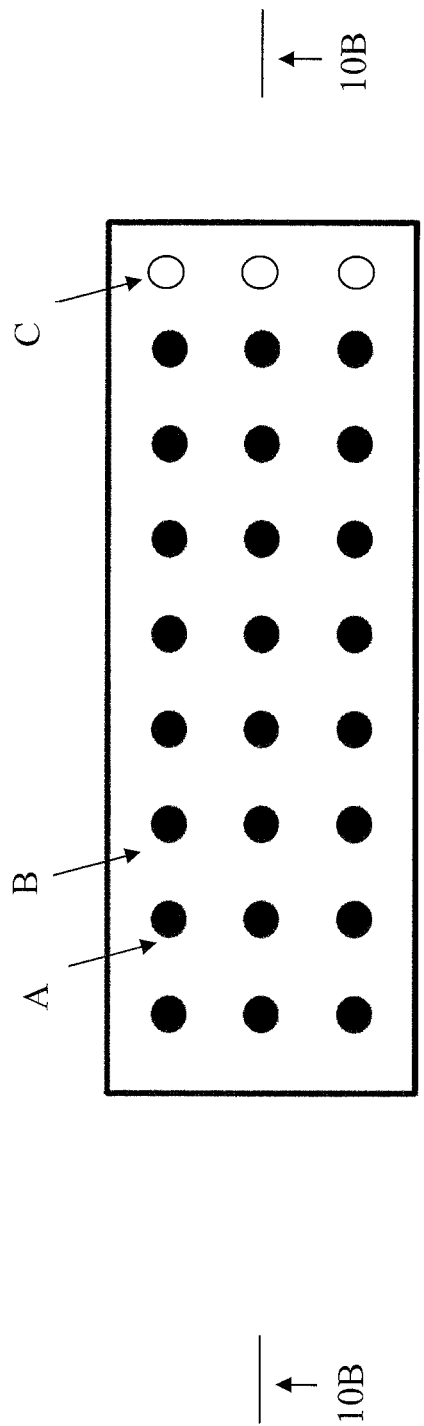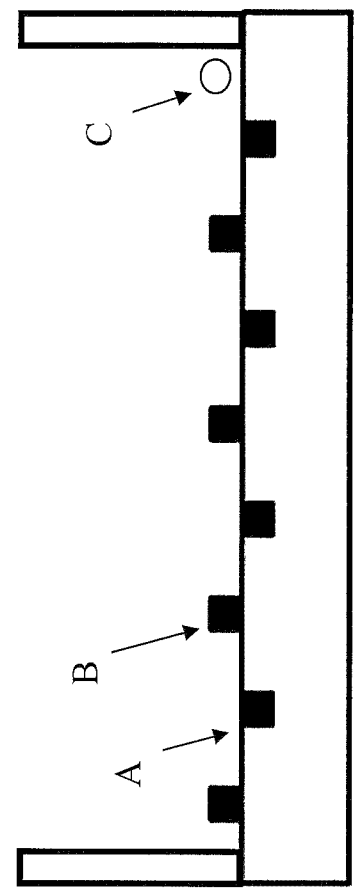
FIG. 10A
FIG. 10B

METHOD AND DEVICE FOR DETECTING BACTERIA AND DETERMINING THE CONCENTRATION THEREOF IN A LIQUID SAMPLE

CROSS-REFERENCE TO RELATED APPLICATIONS

This application is related to U.S. Provisional Application Ser. No. 61/896,877, filed on Oct. 29, 2013, and entitled "Method and Device for Detecting Bacteria and Determining the Concentration Thereof in a Liquid Sample", the disclosure of which is incorporated herein by reference and on which priority is hereby claimed.

BACKGROUND OF THE INVENTION

Field of the Invention

The present invention generally relates to the detection and quantification of particles in a fluid sample, and more specifically relates to a method and device for detecting bacteria and determining the concentration thereof in a liquid sample and, in particular, a urine sample.

Description of the Prior Art

A number of methods are conventionally used to detect and evaluate bacteria in a urine sample. For example, there exist automated analyzers for use in evaluating urine sediment, which mostly utilize flowing a liquid sample through a flow cell and employing either flow cytometry or image analysis of the flowing particles. There are also different types of fluid image capture methods that may be performed, including the optical sectioning methods disclosed in U.S. Pat. No. 8,780,181 (Olesen, et al.) and U.S. Patent Application Publication No. 2012/0244519 (Olesen, et al.).

Alternatively, another conventional method for the detection and evaluation of bacteria in a urine sample involves the manual observations conducted by medical technicians using bright field microscopy. More specifically, this standard method for urine microscopy includes spinning a liquid sample in a centrifuge and discarding the supernatant, leaving only a sediment pellet. The pellet is then re-suspended and evaluated on a microscope slide under a cover slip using a microscope. With this method, the fluid depth is very shallow. For a 30 microliter aliquot with a conventional 22×22 millimeter cover slip, the depth will be approximately 60 microns, and spacing is confined to a more two dimensional space than the three dimensional volume provided by a deeper fluid channel. Such methods, of course, are time consuming and tedious for the medical technician, and often lead to erroneous results in quantifying the bacteria present in the sample due to the small size of the bacteria and limitations of bright field microscopy.

Urine sediment analysis using imaging techniques must detect bacteria in a urine sample in the presence of small non-bacteria debris. This requirement poses challenges, since bacteria are approximately one micron in size, which is near the limit of detection of air-coupled bright field microscopic imaging techniques. With this restriction, bacteria can be seen, but geometric properties cannot be determined, since each bacterium may be represented by only a single pixel due to its size. This limitation makes it difficult to determine the difference between bacteria and small debris (non-bacteria) particles. This difficulty is also present in standard bright field microscopy, where it can be difficult for a technician to identify a specific particle as bacteria or not, even with 400× magnification. There are other techniques that are used, including evaluating the uniformity of particle sizes and positions within the fluid, as well as colony formations that are indicative of bacteria. If bacterial presence is to be confirmed, then alternate techniques such as dry, stained slides that are evaluated under bright field microscopy or quantitative culture are employed to confirm the presence of bacteria.

The difficulties described above with conventional techniques call for a more reliable bacteria detection technique in a debris-filled urine environment.

OBJECTS AND SUMMARY OF THE INVENTION

It is an object of the present invention to provide a method of evaluating bacteria in a bulk fluid.

It is another object of the present invention to provide a method of using the characteristics of bacteria as a means to differentiate bacteria from non-bacteria.

It is still another object of the present invention to provide a highly sensitive and selective method for detecting bacteria in a urine medium.

It is a further object of the present invention to provide a method which measures the average spacing between bacteria to estimate bacteria concentration in place of attempting to count bacteria.

It is yet a further object of the present invention to provide a consumable device which separates bacteria from small debris particles in a urine sample so as to aid in the determination of the concentration of bacteria in the urine sample.

In accordance with one form of the present invention, a method for detecting bacteria and determining the concentration thereof in a liquid sample includes the steps of taking one or more optical sections through a preferably consumable (i.e., discardable) container containing a volume of the liquid sample at a predetermined field of view and at a predetermined focal plane depth or angle and after a predetermined period of time has elapsed to allow non-bacteria debris in the sample to have settled to the bottom of the container. It has been found that, after the predetermined period of time has elapsed, the bacteria have auto arranged in the liquid sample, forming a lattice-like grid pattern uniformly spaced in three dimensions substantially throughout the majority of the liquid sample (except, in some cases, in a no-bacteria zone near the surface of the consumable container that holds the liquid sample). Thus, an optical section through the volume of auto-arranged bacteria may be used to measure the quantity of bacteria residing in that section. By knowing the total volume of the liquid sample held by the container, one can calculate from the measured bacteria residing in the optical section at least an approximation of the total bacteria within the contained volume.

To help carry out the method of the present invention, a consumable container is disclosed herein for holding the liquid sample, the particular structure of which aids in separating the non-bacteria "debris" from the bacteria. In one form, the consumable container includes a recessed bottom portion adjacent to an unrecessed bottom portion. The non-bacteria debris will settle out of the liquid sample into the recessed bottom portion. The focal plane of the optical system of the fluid imaging device is set to near or at the level of the unrecessed bottom portion of the container so that only bacteria that have not settled are detected.

In another form of the present invention, the consumable container which holds the liquid sample defines a relatively long channel having one or more periodically spaced apart projections, or "speed bumps", extending upwardly from the container bottom and partially into the volume of liquid sample held thereby. The projections cause only those particles, such as the auto-arranging bacteria, that are high in the fluid depth to continue to flow down the channel. The regions between adjacent protrusions provide areas for interrogation where particles of specific density ranges will accumulate.

These and other objects, features and advantages of the present invention will be apparent from the following detailed description of illustrative embodiments thereof, which is to be read in connection with the accompanying drawings.

BRIEF DESCRIPTION OF THE DRAWINGS

FIGS. 10A and 10B are respectively a simplified top view and cross-sectional view, taken along line 10B-10B of FIG. 10A, of a ninth embodiment of a consumable container formed in accordance with the present invention to aid in carrying out the method of the present invention for detecting bacteria and determining the concentration thereof in a liquid sample, the container having a plurality of quality assurance shapes formed in the bottom of the container.

DETAILED DESCRIPTION OF THE PREFERRED EMBODIMENTS

Figure 1B:
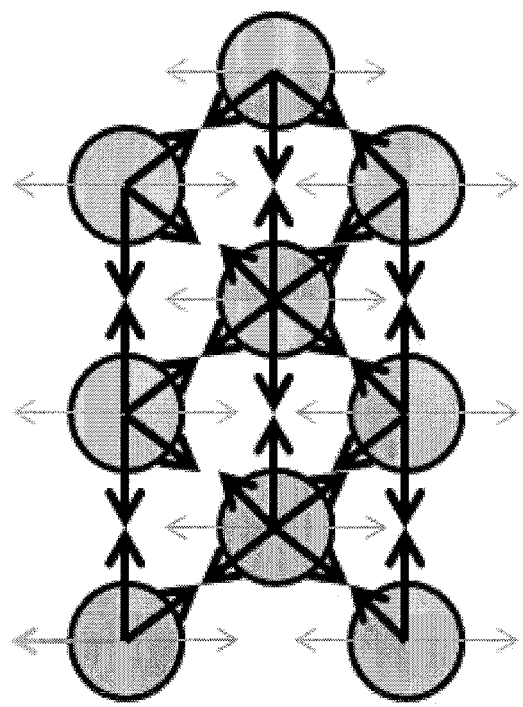
FIGS. 1A and 1B are free body diagrams (pictorial illustrations) of a bacterium in a urine sample containing no other bacteria (FIG. 1A) and in the presence of other bacteria in the urine sample (FIG. 1B), to help facilitate the understanding of the forces associated with each bacterium and how these forces interact with those of neighboring bacterium and which cause the bacteria to auto arrange and remain in suspension within the liquid sample.

Through experimentation, it has been found that bacteria in a liquid sample exhibits some characteristics that may be used to differentiate bacteria from non-bacteria "debris". In particular, two observations have been made concerning bacteria. One relates to the capacity of bacteria to auto arrange in the bulk of a fluid sample, meaning that the bacteria form a lattice-like grid pattern uniformly spaced in three-dimensions throughout the majority of the fluid sample. In addition, as other particles, such as macro particles, including red blood cells, white blood cells, crystals and other small debris, settle to the bottom of the container which holds the liquid sample, the bacteria tend to stay suspended in the majority of the fluid sample. Through further experimentation and supporting theory, it is believed that the aforementioned is a reliable and reproducible characteristic of bacteria and non-bacteria and may be used as an important factor in determining whether bacteria is present in a liquid sample and to measure the concentration of bacteria in the sample.

An additional phenomenon which was observed through experimentation is that the auto-arranged bacteria also generally reside outside a "no-bacteria zone" near the surface of the consumable container that holds the liquid sample, such as a urine sample. Some bacteria, it has been learned, tend to have an "aversion", possibly due to repulsive forces, to surfaces and, in particular, polymer surfaces. This factor also may be taken into account when determining the presence and concentration of bacteria in the liquid sample.

More specifically, it has been found that bacteria generally demonstrate uniform particle sizing and uniform distribution throughout a liquid sample, such as a urine sample. This observation is in contrast with other small debris particles that may be found in urine samples that tend to cluster together and have irregular shapes. By using microscopic imaging methods, such as those disclosed in the aforementioned Olesen, et al. published U.S. application (U.S. Patent Application Publication No. 2011/0261164), the disclosure of which is incorporated herein by reference, it has been found that bacteria in a urine sample are not only uniformly distributed in the focused plane, but also into the bulk or majority of the fluid sample.

After a predetermined period of time, such as between about three minutes and about ninety minutes, preferably about three minutes to about ten minutes, it was determined that bacteria separate from the settled elements, such as red blood cells, white blood cells and crystals, and remain in suspension throughout the majority of the volume of the urine sample. The focal plane of the camera of the fluid imaging device used in such experimentation was set to be within the bulk of the fluid and not at the bottom of the consumable container, such as at 100 microns from the bottom of the container. Visual information from the optical sectioning performed on the urine sample provides visual confirmation that bacteria remain in solution within the bulk of the fluid and, furthermore, that the bacteria auto arrange throughout the majority of the urine sample, except near the bottom and side surfaces of the container. This phenomenon is particularly present when the container is made from a polymer material. Most non-bacterial particles appear to settle at a fall rate of about 100 microns per minute.

These are key differentiating factors that may be employed to separate bacteria from non-bacteria in a reliable and reproducible manner and used in detecting and evaluating bacteria and determining the concentration thereof in a liquid sample. More specifically, these two phenomena will have different implications in the detection and quantification of bacteria in a urine sample. The auto arrangement of the bacteria provides a means to reliably detect the presence of bacteria, while the no-bacteria zone provides a means to separate one form of bacteria from another, such as rod-shaped bacteria, or "rods", for example, bacilli, from spherical shaped bacteria, or coccus, for example, *streptococcus* and *staphylococcus*. Through experimentation, it has been found that not only *staphylococcus* bacteria, but also *proteus, klebsiella, enterococcus, enterobacter* and *Escheri-* chia coli (*E. coli*) forms of bacteria were not only uniformly distributed within the focal plane of the imaging camera, but also throughout a majority of the urine sample.

Auto arrangement is the term used herein to describe the physical distribution of bacteria within a three-dimensional bulk of the urine sample. Bacteria (rods and cocci) have a natural tendency to uniformly distribute within the fluid. Motility does not appear to be a driving force for this separation; however, there appear to be other forces present which cause the bacteria to auto arrange and maintain their positioning within the volume of urine sample even in the presence of gravity (for these particles, the force due to gravity will be approximately twice the buoyant force based on the equations set forth in FIG. 1A and is on the order of $10^{-15}$ Newtons).

Figure 1A:
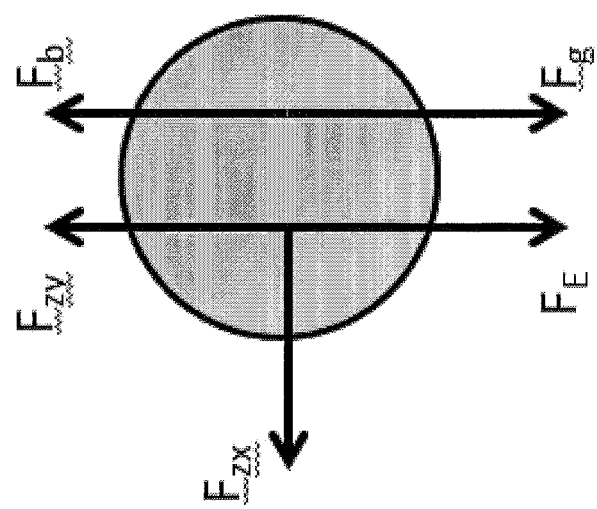

More specifically, FIGS. 1A and 1B illustrate free body diagrams of a bacterium in a urine sample as well as represented as part of a lattice structure (representing the uniform distribution commonly seen with spacing generally ranging from about 10 to about 60 microns between bacteria). In order for the system to maintain equilibrium, the upward and downward forces must match, causing a net zero force, and the bacteria will then maintain the stable, uniform lattice-like structure. Such a lattice-like structure always tends toward a state of minimum energy, and the bacteria will tend to fill all sites in the minimum lattice structure defined by the model shown in FIG. 1B. In FIG. 1B, the lighter arrows represent gravity and buoyancy, and the darker arrows represent Zeta Potential forces. Thus, and as shown in FIG. 1B, several bacteria in a sample will have interactions, causing an auto arrangement and will inhibit settling. In other words, equal and opposite forces will maintain a static structure that will auto arrange without settling. For reference, *E. coli* bacteria will each have a mass in the range from about 2.9 to about $9.5 \times 10^{-13}$ grams, resulting in approximately 3 to about $9 \times 10^{-15}$ Newtons of gravitational force.

As is illustrated by FIG. 1A of the drawings, there are several forces associated with each bacterium, and these forces interact with the forces of each neighboring bacterium that cause the system to maintain a uniform equilibrium. More specifically, a zeta potential force in the x-direction (Fzx) is associated with a bacterium; a zeta potential force in the y-direction (Fzy) also acts on the bacterium; a buoyant force (Fb) acting on a bacterium has been determined to be equal to the density of the fluid multiplied by the volume multiplied by g (gravity); a gravitational force (Fg) acting on the bacterium is equal to the mass of the bacterium multiplied by g (gravity); and an electric field force (Fe) is further associated with the bacterium. With no other Zeta Potential sources, Fz is zero and if the electric field force Fe is also zero, then the only other forces acting on the bacterium are buoyancy and gravity; under such circumstances, settling should occur.

The electrical force is commonly described by the theories associated with the zeta potential. The zeta potential is defined by a fluid region surrounding a particle containing ions that are loosely bound. The zeta potential is the driving force in colloidal systems (fluids with finely dispersed solids within, such as urine). The magnitude of the zeta potential determines if the system is stable (particles maintain structure) or unstable (particles will settle or float depending on the specific gravity of the fluid). The system (cell and surrounding fluid) will be electrically neutral from a macroscopic perspective, since counter-ions (ions with opposite charge to the bound charge on the particle surface) will surround the cell in a small layer that generally is no larger than a few tens of nanometers. The natural negative charge for a bacteria is a byproduct of the cell acting as a "proton pump" as part of ATP (adenosine triphosphate) conversion for energy. The bacteria will actually try to create a pH gradient across its membrane wall to facilitate ATP transfer and this causes the net negative charge of the bacteria. Add to that the zeta potential found from the ionized urine sample and there is a lot of electrical activity, which is an important consideration in cases where bacteria is in a water environment (or other non-ionic fluid) and the function still exists due to the proton pump (the repulsion force will be slightly reduced). Within the fluid, the particles and the counter-ions will have a local charge that can act to repel other like particles and maintain dispersion. As shown in the free body diagrams of FIGS. 1A and 1B, the zeta potential is the largest driving factor for a urine colloidal system. Most particles in urine will not have sufficient zeta potential to overcome the settling forces due to gravity, since the particle mass will be large with respect to the forces from zeta potential and the particles will settle. However, bacteria have a small particle mass, and the zeta potential is large enough to keep the colloidal system in suspension. The method of the present invention takes advantage of this auto arrangement phenomenon of bacteria and uses it to detect and evaluate bacteria and to determine the concentration thereof in a urine sample.

More specifically, a method for detecting bacteria and determining the concentration thereof in a liquid sample includes the steps of taking one or more optical sections through a consumable (i.e., discardable), preferably polymer container containing a volume of the liquid sample at a predetermined field of view and at a predetermined focal plane depth or angle, and after a predetermined period of time (such as about three minutes to about ten minutes or more) to allow non-bacteria debris in the sample to have settled to the bottom of the container. After the predetermined period of time has elapsed, the bacteria has auto arranged in the liquid sample, forming a lattice-like grid pattern uniformly spaced in three dimensions, substantially throughout the majority of the liquid sample (except, in some cases, in a "no-bacteria zone" near the polymer surface of the consumable container that holds the liquid sample). Thus, an optical section through the volume of auto-arranged bacteria may be used to measure the quantity of bacteria residing in that section. Knowing the total volume of the liquid sample held by the container, one can calculate at least an approximation of the total bacteria within the contained volume.

Optical sectioning may occur vertically through the liquid sample, horizontally at different heights within the volume, or at an angle to the vertical or horizontal through the liquid sample, as taught by the aforementioned Olesen, et al. published U.S. application. When such a slanted optical sectioning of the sample is performed, the preferred angle with respect to the vertical of the optical sectioning is about seven (7) degrees. Since non-bacteria "debris" settles to the bottom of the container after the predetermined period of time has elapsed, a horizontal optical sectioning may be performed with the focal plane of the system camera disposed about various depths, such as 50 microns, 100 microns and 150 microns above the container bottom.

When one or more optical sections of the liquid sample held by the container have been performed, the number of bacteria found in each section may be quantified and may be averaged. By knowing the camera's depth of field, or stated another way, the depth of the optical section in which bacteria appearing in the section are in focus and may be identified as residing in that section, and by knowing the volume of liquid sample held by the container, the averaged number of bacteria from the sample optical sections, multiplied by the number of optical sections within the width, depth or diagonally through the volume of liquid sample, will yield at least an approximation of the total number of bacteria for a given volume of sample held by the container (e.g., bacteria count per microliter). The measurements and calculations may be performed in accordance with the method automatically by the imaging instrument and without the need for any tedious or manual evaluations on the part of a medical technician which are prevalent with the use of conventional methods, such as by using bright field microscopy.

Alternatively, again through optical sectioning, measurements may be performed to estimate the average spacing between bacteria. This average particle spacing may be used as a means to estimate the bacteria concentration in the volume of liquid sample held by the container, in place of attempting to count bacteria. More specifically, it may not be necessary to count the bacteria (in order to have increased confidence that non-bacteria has settled) but can then use statistics to determine the distances between bacteria in a single focal plane. The distances are then averaged and an algorithm can be used to look at different focal depths to ensure that the auto-arrangement is complete or at least indicative of bacteria and not non-bacteria. The method of determining the average spacing between bacteria (or other particles) includes evaluating all of the areas that represent bacteria in an image and evaluating their focus curves (the angled optics provide an object stack of in- and out-of-focus images) that can be used to measure the optical distance between particles that are in the same focal plane. This procedure is repeated across all focal planes and a 3-d map of particles can be generated based on the average statistics.

As mentioned previously, there appears to be a "no-bacteria zone" situated near the surfaces of containers formed of a polymer material. Just like bacteria, polymers have a zeta potential in a fluid medium. Such polymers include an acrylic material, such as poly (methyl methacrylate), or PMMA, which is preferably the material from which the consumable container of the present invention is made.

Figure 11B:
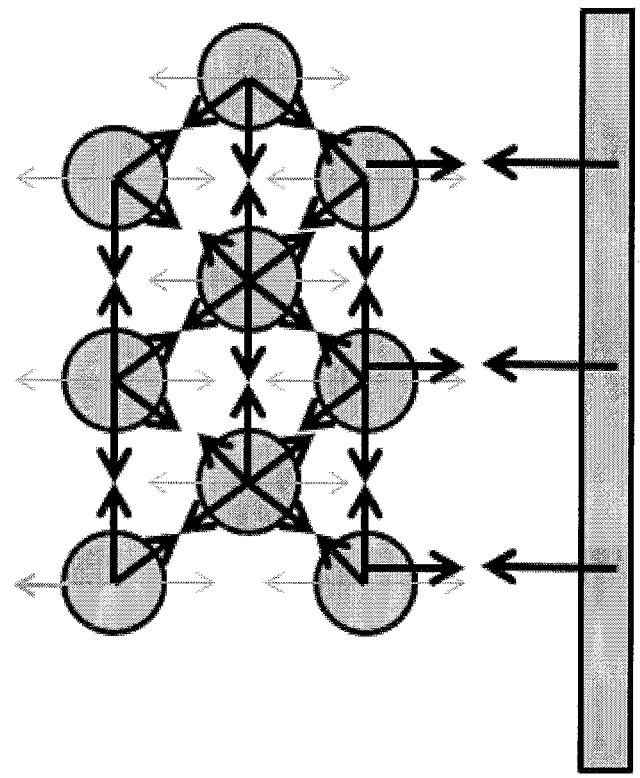
FIGS. 11A and 11B are free body diagrams (pictorial illustrations) of a polymer substrate and associated bacteria, and the forces associated with each, in a urine sample.
Figure 11A:
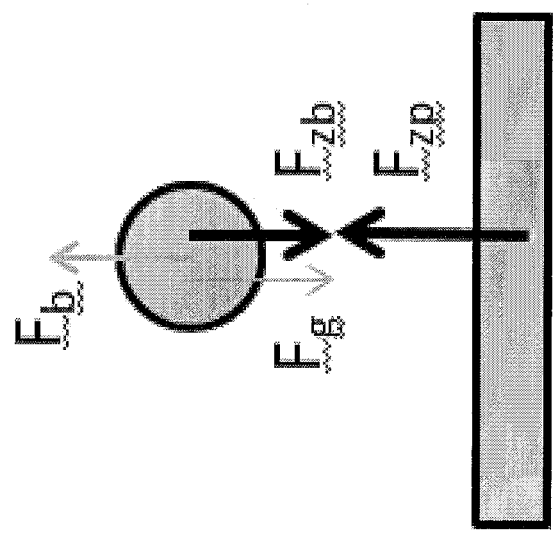

FIGS. 11A and 11B are free body diagrams of a polymer substrate and associated bacteria. Shown in FIG. 11A are the forces associated with a bacterium and a polymer surface. The term Fzb represents the zeta potential force for bacteria; the term Fzp represents the zeta potential force for a polymer substrate; the term Fb represents the buoyant force, which is equal to the density of the fluid sample multiplied by the volume of the bacteria multiplied by g (gravity); and the term Fg represents the force of gravity, which is equal to the mass of the bacterium multiplied by g (gravity). It is clear from FIG. 11A that equal and opposite forces will maintain a static structure that will allow the bacteria to auto arrange without settling. Furthermore, the consumable container's zeta potential will create a "no-bacteria zone" near the surface of the polymer, which will occur both at the top and bottom of the container, and at the sides thereof. Furthermore, rod bacteria are larger than coccus bacteria and will have more mass and are more likely to overcome the zeta potential with gravity and have at least partial settling, or at least will exhibit a different "no-bacteria zone" thickness, since gravity will overcome more of the electric force.

As shown in FIG. 11B, several bacteria in a sample will have interactions, causing auto arrangement, and will inhibit settling and will maintain a "no-bacteria zone" near the surface of the polymer consumable container.

Accordingly, once non-bacteria debris has been separated from bacteria within the urine sample, an optical sectioning of the liquid sample with a focal plane in proximity to the bottom (and top) of the polymer container, and with further optical sectioning a relative distance from the top and bottom of the polymer container, will lead to a determination and evaluation, and at least an approximate concentration, of different types of bacteria within the urine sample, since some bacteria, such as the higher mass rods, will occupy the "no-bacteria zone", while coccus bacteria, which have less mass and which are less likely to overcome the zeta potential with gravity, will remain in suspension and outside of the "no-bacteria zone" and will auto arrange within the volume of the liquid sample.

FIGS. 2-10 of the drawings depict various forms of consumable containers for holding a liquid sample, formed in accordance with the present invention, the particular structures of which aid in separating the non-bacteria "debris" from the bacteria and which help carry out the method of the present invention for detecting bacteria and determining the concentration thereof in a liquid sample. Preferably, the container is formed as a consumable product, that is, it is discardable after use, and is made from a polymer material, such as acrylic PMMA.

Figure 2:
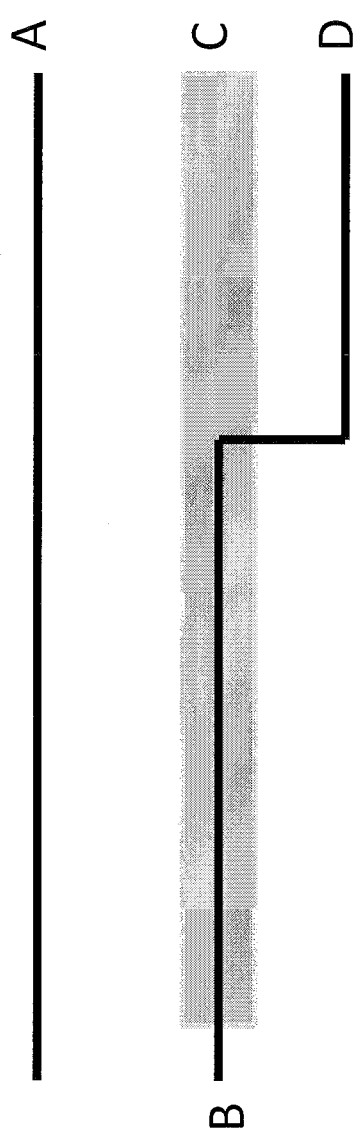
FIG. 2 is a simplified cross-sectional view of a first embodiment of a consumable container formed in accordance with the present invention to aid in carrying out the method of the present invention for detecting bacteria and determining the concentration thereof in a liquid sample.

FIG. 2 is a simplified cross-sectional view of a consumable container formed in accordance with the present invention. In FIG. 2, reference letter A represents the container top surface; reference letter B represents the container bottom surface; reference letter C represents the focal depth of the camera of the imaging system which takes an optical section through the liquid sample held by the container; and reference letter D represents the container bacteria zone bottom surface.

More specifically, the container of FIG. 2 includes a recessed bottom portion and an unrecessed bottom portion adjacent to the recessed bottom portion. The non-bacteria debris will settle out of the liquid sample into the recessed bottom portion. The focal plane of the optical system of the fluid imaging device is set to near or at the unrecessed bottom portion of the container so that only bacteria are detected. Thus, the optical system will scan for particles that reside over the non-recessed bottom portion of the container. Incorporating a separate region, at D, where the container bottom is lower than the focal plane of the optical system will realize a condition where settled particles will not be in view, leaving only bacteria for counting (after waiting the appropriate settling time).

Figure 3:
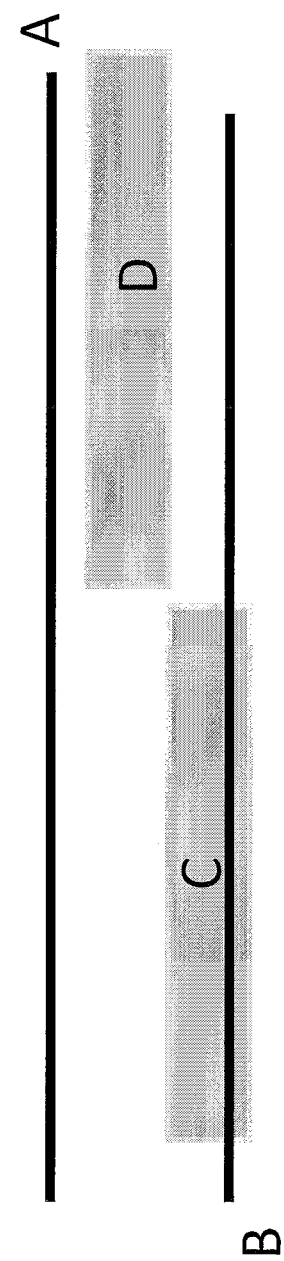
FIG. 3 is a simplified cross-sectional view of a second embodiment of a consumable container formed in accordance with the present invention to aid in carrying out the method of the present invention for detecting bacteria and determining the concentration thereof in a liquid sample.
Figure 4:
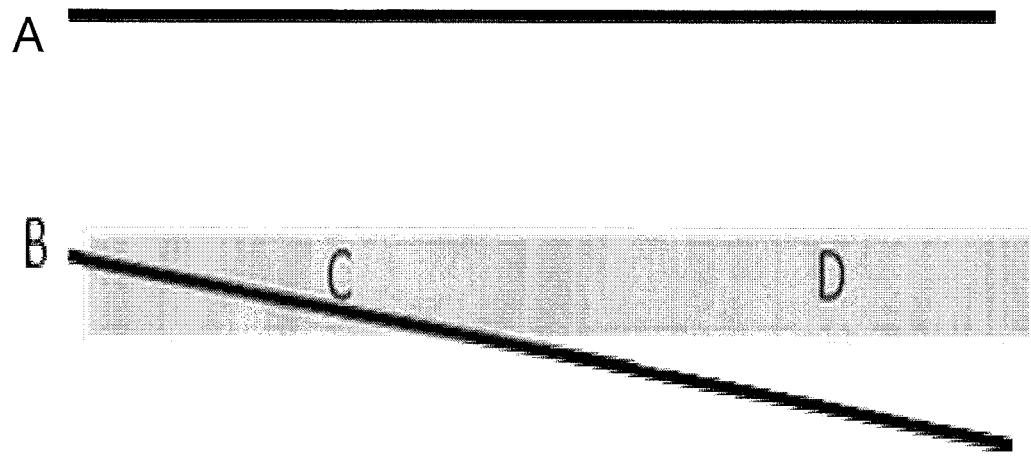
FIG. 4 is a simplified cross-sectional view of a third embodiment of a consumable container formed in accordance with the present invention to aid in carrying out the method of the present invention for detecting bacteria and determining the concentration thereof in a liquid sample.
Figure 5:
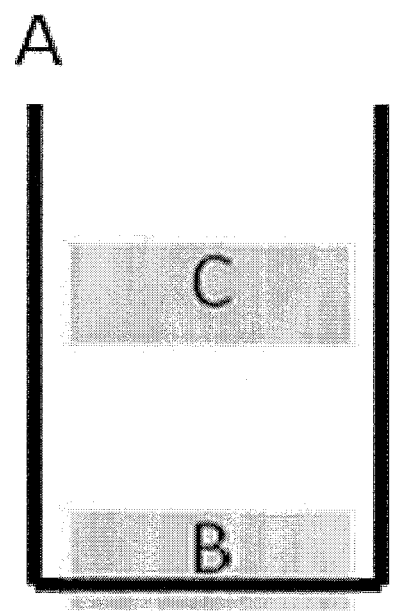
FIG. 5 is a simplified cross-sectional view of a fourth embodiment of a consumable container in the form of an open-topped microtiter plate well formed in accordance with the present invention to aid in carrying out the method of the present invention for detecting bacteria and determining the concentration thereof in a liquid sample.

FIGS. 3-5 represent other embodiments of a container for use with the method of the present invention, which utilize the natural separation of bacteria from non-bacteria in a fluid. More specifically, FIG. 3 is a simplified cross-sectional view of another form of a container formed in accordance with the present invention. Again, reference letter A represents the container top surface; reference letter B represents the container bottom surface; reference letter C represents the camera focal depth for settled particles; and reference letter D represents the camera focal depth for bacteria. In the particular embodiment shown in FIG. 3, the container top and bottom surfaces are parallel to each other, but optical interrogation occurs at different depths within the fluid. Heavier particles ("debris") settle out of the liquid sample and reside at the bottom surface of the container, that is, at the "C" camera focal depth, whereas the bacteria, which auto arrange, occupies higher levels relative to the bottom of the container in the volume of liquid sample and are captured at the camera focal depth located at "D".

FIG. 4 is a simplified cross-sectional view of yet another embodiment of a container formed in accordance with the present invention, where reference letter A represents the container top surface; reference letter B represents the container bottom surface; reference letter C represents the camera focal depth for settled particles; and reference letter D represents the camera focal depth for bacteria. As one can see from FIG. 4, the container includes a bottom surface which is sloped to the horizontal so that interrogation at a fixed vertical position (at "C", which is close to the sloping bottom surface of the container at the shallower section thereof) will detect settled particles, whereas interrogation at fixed vertical position "D" (which is effectively at a higher level from the sloping bottom surface, even though it is within the same focal plane as focal depth "C") will detect just bacteria in the liquid sample.

FIG. 5 is a simplified side view of a further embodiment of a container formed in accordance with the present invention for carrying out the method of detecting and quantifying bacteria in a liquid sample. In FIG. 5, reference letter A represents a container; reference letter B represents the camera focal depth for settled particles; and reference letter C represents the camera focal depth for bacteria. The container shown in FIG. 5 is preferably an open-topped, microtiter plate well, and the optical system used for performing optical sections of the volume of liquid sample contained therein interrogates the fluid at different depths. The camera focal depth at "B" is near or at the bottom of the well and detects settled particles, whereas the camera focal depth at "C", which is raised above the bottom of the well, detects bacteria which are in an auto arrangement.

Figure 6:
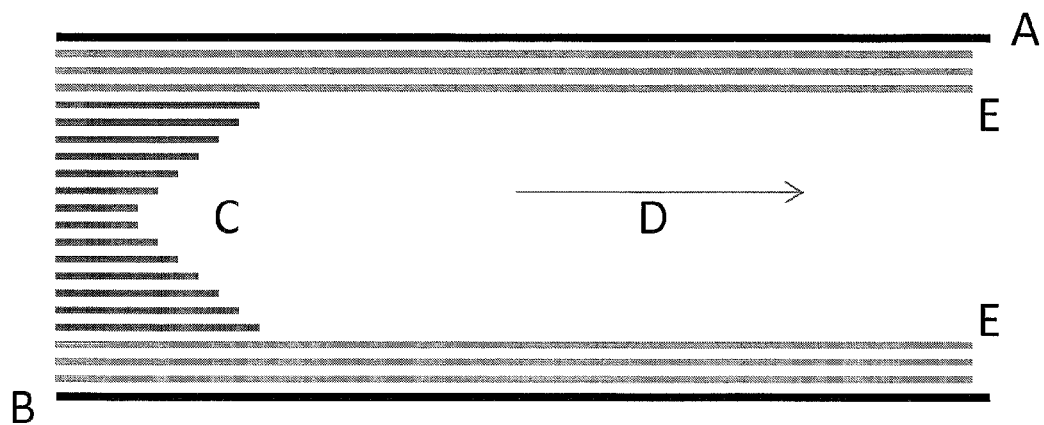
FIG. 6 is a simplified top view of a fifth embodiment of a consumable container formed in accordance with the present invention to aid in carrying out the method of the present invention for detecting bacteria and determining the concentration thereof in a liquid sample, the container including a plurality of flow channels to promote capillary flow of the liquid sample therethrough.

FIG. 6 is a simplified top view of another form of a container constructed in accordance with the present invention and used to carry out the method for detecting bacteria and determining the concentration thereof in a liquid sample. More specifically, reference letter A represents the container left surface; reference letter B represents the container right surface; reference letter C denotes the fluid flow start region; reference letter D, in the form of an arrow, represents fluid flow through the container; and reference letter E represents fluid flow channels formed in the container. The fluid flow channels may be defined by of a series of parallel plates extending vertically upwardly from the bottom surface of the container toward the top surface, between the left and right surfaces thereof. The flow channels within the container, situated between adjacent plates, promote capillary flow of the fluid.

In the preferred form of the container shown in FIG. 6, there are several fluid flow channels, defined by parallelly disposed plates, formed inwardly of and in proximity to the left surface of the container and the right surface of the container, and these left and right side fluid flow channels extend axially along the length of the container. There are also parallelly disposed fluid flow channels spaced apart from one another and extending entirely across the width of the container, from the left surface to the right surface thereof, near the fluid flow start region C. These channels are also defined by adjacent plates, and may extend with mutually increasing axial lengths near region C from the longitudinal center of the container in symmetrical directions outwardly towards the left and right surfaces thereof.

Thus, the flow features incorporated in the container increase the surface area (with respect to fluid volume) and provide a guide for fluid flow.

Alternative structure to promote fluid flow in the container of FIG. 6 may include reducing the fluid channel dimensions (width and depth) to provide an increased surface area with respect to volume and to promote capillary flow. Alternatively, the material from which the plates defining the channels are formed may be selected with sufficient contact angle (hydrophilicity) to support capillary action through the container. Furthermore, surface treatments on the left and right surfaces of the container and on the surfaces of the plates defining the channels therebetween may be performed to promote fluid flow through the container, and such treatments include plasma treatment, corona treatment, surface chemistry reactions or surfactant applications. These embodiments will utilize capillary action for flow of the fluid into and through the container. Further alternative approaches to promote fluid flow into and through the container are envisioned to include an open system, where the fluid is merely dropped or deposited onto the container, or a closed system, where the fluid is mechanically pumped into the container.

Figure 7:
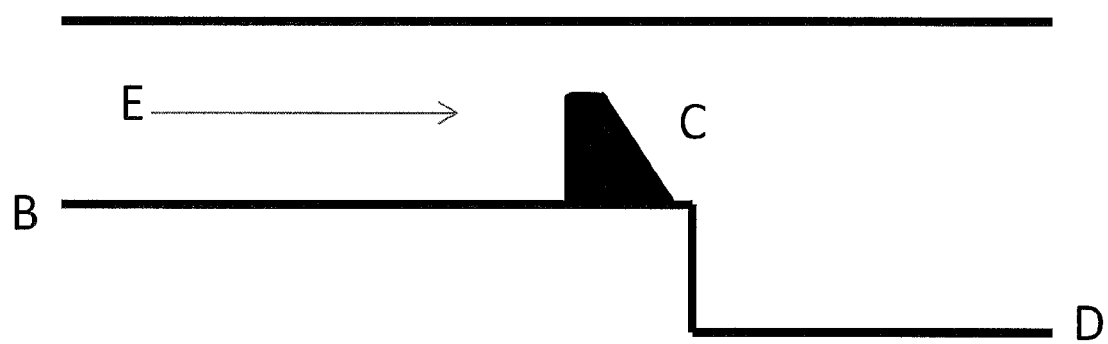
FIG. 7 is a simplified cross-sectional view of a sixth embodiment of a consumable container formed in accordance with the present invention to aid in carrying out the method of the present invention for detecting bacteria and determining the concentration thereof in a liquid sample.

A simplified cross-sectional view of a modification to the container illustrated in FIG. 2 is shown in FIG. 7 of the drawings. Reference letter A in FIG. 7 represents the container top surface; reference letter B represents the non-recessed bottom surface of the container; reference letter D represents the recessed, bottom surface of the container defining a bacteria detection zone; reference letter E, in the form of an arrow, represents fluid flow through the container; and reference letter C represents a projection which extends upwardly from the container bottom and partially into the volume of liquid sample held thereby. The projection acts as a "speed bump" with respect to the flow of fluid axially through the container, as shown by reference letter E. (It should be understood that the term "speed bump" is used herein to facilitate an overall understanding of the invention; however, it should be realized that the fluid will actually progress at a faster rate over the protrusion since the volume flow is constant and the cross-sectional area is small at the "speed bump".) The projection C stops denser particles from continuing down the container and flowing into the bacteria zone, at "D". Thus, as with the container shown in FIG. 2, this particular container shown in FIG. 7 includes a non-recessed bottom surface, at B, followed by an adjacent recessed bottom surface, at "D", which defines a "trench" in which bacteria in an auto arrangement resides after flowing over the projection C.

Preferably, the container shown in FIG. 7 defines a relatively long channel axially therethrough in which fluid may flow. As the fluid flows down the channel defined by the container, particles will be settling out of the liquid sample, and the denser particles will concentrate at the beginning of the channel, before the projection C, and less dense particles will settle further downstream of the container channel. This phenomenon can be amplified by applying flow features within the channel that sort elements by size or by vertical position within the channel.

Figure 8:
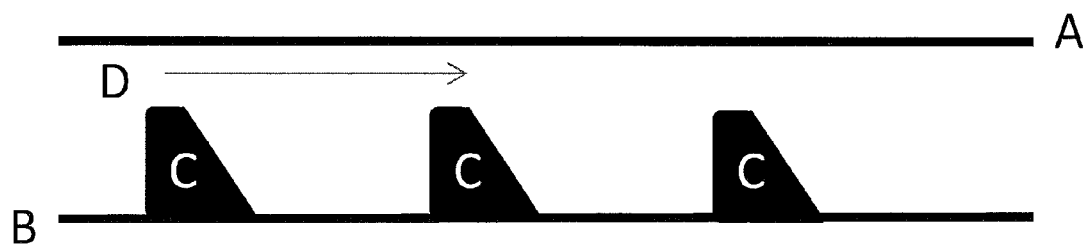
FIG. 8 is a simplified cross-sectional view of a seventh embodiment of a consumable container formed in accordance with the present invention to aid in carrying out the method of the present invention for detecting bacteria and determining the concentration thereof in a liquid sample.

More specifically, a variation of the container illustrated by FIG. 7 is shown in FIG. 8 of the drawings, but without a recessed bottom surface. In FIG. 8, reference letter A represents the container top surface; reference letter B represents the bottom surface, which is parallel to the top surface; reference letter C represents a projection extending upwardly from the container bottom surface and partially into the volume of liquid sample held thereby; and reference letter D represents the direction of fluid flow, by an arrow, axially through the container. Thus, as can be seen from FIG. 8, this particular container of the present invention includes a plurality of periodically spaced apart projections, or "speed bumps", over at least a portion of the axial length of the container. These projections C situated at intervals along the length of the container will cause only those particles that are high in the fluid depth to continue down the channel defined by the container and provide areas for interrogation where particles of specific density ranges will accumulate.

Figure 9:
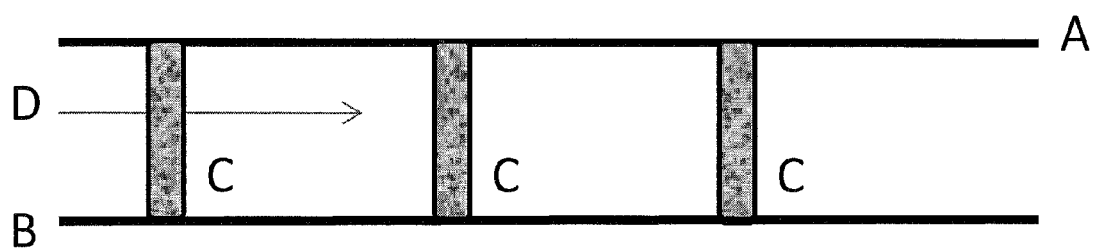
FIG. 9 is a simplified cross-sectional view of an eighth embodiment of a consumable container formed in accordance with the present invention to aid in carrying out the method of the present invention for detecting bacteria and determining the concentration thereof in a liquid sample.

FIG. 9 illustrates yet another form of a container for carrying out the method of the present invention for detecting and determining the concentration of bacteria in a liquid sample. The embodiment shown in FIG. 9 is similar to that shown in FIG. 8, except that the projections C in FIG. 8 are replaced by different sized filters in the embodiment of FIG. 9. In FIG. 9, reference letter A represents the container top surface; reference letter B represents the container bottom surface, which includes no recessed portion; reference letter D represents the direction of fluid flow, by an arrow, axially through the container which, like the container of FIG. 8, defines a relatively long channel for fluid flow; and reference letter C represents filters in place of the projections.

More specifically, and as shown in FIG. 9, there are a plurality of filters which extend between the bottom surface and the top surface of the container and through which the liquid sample flows in the direction D. The filters are spaced apart from one another over at least a portion of the axial length of the container, in the same manner as the projections are spaced in the embodiment of FIG. 8. Filters of different pore sizes are preferably used. More specifically, the upstream filters have preferably a larger pore size than downstream filters, so that the filters decrease in pore size in the direction of fluid flow D. The filters will block particles having different dimensions so that such particles will accumulate in regions between filters, and these regions may be interrogated by optical sectioning or the like to detect and evaluate the types of particles accumulating in each region. The smaller particles such as bacteria, being one micron in size, will pass through all of the filters and will accumulate in a region in the downstream end of the container, where such bacteria may be determined and quantified.

FIGS. 10A and 10B are respectively a simplified top view and a cross-sectional view of a container, and illustrate a plurality of spaced apart recesses or projections, or particles, formed in or on the bottom surface of the container for quality assurance purposes. An optical evaluation of a fluid should include references to ensure the system is in focus, magnification is appropriate and optical features are resolved appropriately. These features (not drawn to scale) represent standard elements in the fluid sample and provide both a focus reference and a means to ensure the optics are functioning properly if the sample is from a healthy host without formed elements. A preferred embodiment for these features, as illustrated by FIGS. 10A and 10B, will be to incorporate them into or near the container bottom surface at the optimal focal position. Such features can be shapes, and may include a roughened surface, that may be incorporated when the consumable container is fabricated, for example, molded into the bottom surface of the container, or in a close fabrication process, such as where the feature is laser marked on the container, for example, or as fixed beads or latex particles, for example, situated at the bottom surface of the container. The features will be located at optimal focus so that any sample can be analyzed with appropriate confidence in the optical system. Negative results after testing urine samples, where no bacteria or other particles are detected, will be verified as being accurate when only the quality assurance features are identified and nothing else. In FIGS. 10A and 10B, the letter "A" represents recesses, the letter "B" represents projections, and the letter "C" represents particles.

The simplified top view of the container shown in FIG. 10 is one possible implementation of such quality assurance features. The size, shape, contrast, position and spacing of such projections, recesses or particles are designed to ensure optical clarity and discrimination of the elements of interest.

Still another form of a container for carrying out the method of the present invention for detecting and determining the concentration of bacteria in a liquid sample is shown in FIGS. 24-28 of the drawings. Generally, the container is in the form of an elongated member 2 having a handle portion 4 and a read area portion 6 (where imaging of the sample takes place) that extends axially outwardly from the handle portion 4. The handle portion 4 and the read area portion 6 comprise the housing of the sample container. As in the other embodiments of the sample container described previously, this particular embodiment is also manufactured to be a consumable component, that is, after use, the sample container is disposed of in accordance with required safety protocols.

An inlet port 8 for receiving a liquid sample therein is situated on the top surface of the housing over the handle portion 4 thereof. The inlet port 8 is in fluid communication with an interior, elongated, liquid sample well 10 which extends axially along at least a portion of the length of the read area portion 6 of the sample container. The well 10 holds a liquid sample, such as urine, deposited on the sample container through the inlet port 8, and defines an area on the top and/or bottom surfaces of the housing where imaging of the liquid sample contained in the well 10 occurs.

At the distal end of the read area portion 6 of the housing of the sample container, which is axially opposite the handle portion 4, and in communication with the well 10, is situated a bacteria read area 12. More specifically, the bacteria read area 12 constitutes the end portion of the well 10 containing the liquid sample and preferably includes three or more adjacent sections having progressively increased depths over the axial length of the bacteria read area portion of the well 10, increasing in depth in a direction toward the distal end of the read area portion 6 of the housing, similar in some respects to the sample container shown in FIG. 2 of the drawings (which has two sections of varying depth). An optical system of a fluid imaging device used for imaging the sample container shown in FIGS. 24-28 will scan for particles in one or more sections of the liquid sample well 10, as well as for auto-arranged bacteria residing in the bacteria read area 12. As mentioned previously with respect to the embodiment of the sample container shown in FIG. 2, heavier particles, such as formed elements, which do not auto arrange will settle to the bottom of the well 10, independent of well depth, leaving bacteria for counting in one or more of the bulk sections (i.e., the mid-level section of the sample container well 10, containing the bulk of the fluid) away from the bottom. When the sample container is filled, all of the elements (formed elements, bacteria, debris, lipids, etc.) will be randomly distributed throughout the fluid bulk. Since the bacteria do not settle like most formed elements, they can be more easily viewed and differentiated in the fluid bulk where the formed elements are no longer present. The auto-arranged bacteria is preferably measured in the bacteria read area 12 at the distal end of the well 10.

The bacteria read area 12 of the well 10 preferably includes three sections, that is, a first section 22, a second section 24 adjacent to the first section 22, and a third section 26 adjacent to and following the second section 24, of varying depth. More specifically, the depth of the well 10 over the read area portion 6 is preferably about 250 microns. The first section 22 is preferably about 450 microns in depth, and the bacteria residing therein is read optically at a depth of about 200 microns. The second section 24 is preferably about 650 microns in depth, and the bacteria residing therein is read optically at a depth of about 400 microns. The third section 26 is preferably about 850 microns in depth, and the bacteria residing therein is read optically at a depth of about 600 microns.

To facilitate a full understanding of the present invention, the method and container for carrying out the method disclosed previously herein will now be further described.

In accordance with one form of the present invention, a method for detecting bacteria and determining the concentration thereof in a liquid sample includes the steps of taking at least one optical section through a volume of the liquid sample at a predetermined field of view and at a predetermined focal plane depth or angle in the volume and after a predetermined time has elapsed to allow bacteria in the liquid sample to auto arrange, and counting the number of bacteria present within the at least one optical section. It is also possible to watch the settling phenomena to determine the optimal time for evaluation as an algorithm can be fabricated to determine when settling is complete and the auto-arranging process is the only activity occurring. It is also possible to make a predictive algorithm that does not have to wait until complete separation but instead watches the sample and processes out the particles that are settling and only evaluates the portion of the sample that has bacteria characteristics. The steps of the method also include calculating the number of optical sections into which the volume of the liquid sample may be divided thereby determining a total number of possible optical sections, multiplying the number of bacteria present in the at least one optical section by the total number of possible optical sections thereby determining at least an approximation of the total number of bacteria within the volume of the liquid sample and determining the concentration of bacteria within the liquid sample based on the at least approximation of the total number of bacteria within the volume of the liquid sample.

The predetermined time allowed for bacteria in the liquid sample to auto arrange is preferably between about three minutes and about ten minutes or more. Furthermore, the at least one optical section taken through the volume of the liquid sample preferably has a focal plane angle of about seven degrees relative to a vertical plane through the volume. Alternatively, the at least one optical section taken through the volume of the liquid sample has a focal plane angle of about zero degrees relative to a vertical plane through the volume (that is, the focal plane is vertical), or is about ninety degrees relative to a vertical plane through the volume (that is, the focal plane is horizontal), or an angle therebetween. If the focal plane of the optical section is horizontally disposed through the volume of the liquid sample, then preferably the optical section has a focal plane depth of about 100 microns above the bottom of the volume of the liquid sample. Alternatively, the focal plane depth may be 500 microns, or more, to get rid of halos from large settled objects (a function of the depth of field of the optics and the out-of-focus depth). Or, the focal plane depth of the optical section through the sample container may be at least one of about 100, about 200, about 400, about 600, about 800, about 1,000 and about 1,200 microns above the bottom of the volume of the liquid sample.

In another form of the present invention, a method for detecting bacteria and determining the concentration thereof in a liquid sample includes the steps of taking a plurality of optical sections through a volume of the liquid sample at a predetermined field of view and at one or more predetermined focal plane depths or angles in the volume and after a predetermined time has elapsed to allow bacteria in the liquid sample to auto arrange, and counting the number of bacteria present within each optical section of the plurality of optical sections. The steps of the method further include calculating an average of the number of bacteria present by dividing the total number of bacteria present in the plurality of optical sections by the number of optical sections taken through the volume of the liquid sample thereby determining an average number of bacteria present within the optical sections of the plurality of optical sections, calculating the number of optical sections into which the volume of liquid sample may be divided thereby determining a total number of possible optical sections, multiplying the average number of bacteria present in the optical sections of the plurality of optical sections by the total number of possible optical sections thereby determining at least an approximation of the total number of bacteria within the volume of the liquid sample and determining the concentration of bacteria within the liquid sample based on the at least approximation of the total number of bacteria within the volume of the liquid sample.

In yet another form of the present invention, a method for detecting bacteria and determining the concentration thereof in a liquid sample includes the steps of taking at least one optical section through a volume of the liquid sample at a predetermined field of view and at a predetermined focal plane depth or angle in the volume and after a predetermined time has elapsed to allow bacteria in the liquid sample to auto arrange, and determining the average spacing between bacteria present within the at least one optical section thereby determining the average bacteria spacing. Then, the three dimensional area occupied by the volume of the liquid sample is calculated thereby determining a three dimensional volumetric area, the three dimensional volumetric area is divided by the average spacing between bacteria thereby determining at least an approximation of the total number of bacteria within the volume of the liquid sample and the concentration of bacteria within the liquid sample based on the at least approximation of the total number of bacteria within the volume of the liquid sample is determined.

In still another form of the present invention, a method for detecting particles in a liquid sample and distinguishing a first type of particles from at least a second type of particles in the liquid sample includes the steps of at least partially filling a container with a volume of the liquid sample containing the first type of particles and the at least second type of particles, the container having at least one surface made from a predetermined material which causes the at least second type of particles in the liquid sample to exhibit an aversion thereto and the first type of particles in the liquid sample to exhibit no aversion thereto. The particles of the at least second type of particles in the liquid sample primarily do not occupy an aversion region of the volume of the liquid sample in proximity to the surface of the container, and the particles of the first type of particles in the liquid sample de-net occupy the aversion region of the volume of the liquid sample in proximity to the surface of the container. Then, at least one optical section through the aversion region of the volume of the liquid sample at a predetermined field of view and at a predetermined focal plane depth or angle is taken. The optical section optically detects the particles of the first type of particles occupying the aversion region of the volume of the liquid sample in proximity to the surface of the container, as distinguished from the particles of the at least second type of particles which primarily do not occupy the aversion region.

Preferably, the surface of the container which causes the aversion thereto by the particles of the at least second type of particles is made from an acrylic material, and more preferably is made from poly (methyl methacrylate) (PMMA). Other materials which cause bacteria aversion include, but are not limited to, polystyrene and cyclic olephin polymer (COP).

Now, various forms of a container which may be used to carry out the method of the present invention disclosed herein will now be further described. In one form of the present invention, and as shown in FIG. 2 of the drawings, a container for holding a volume of a liquid sample and used for separating different types of particles within the volume of the liquid sample, the different types of particles within the volume of the liquid sample held by the container including a first type of particles which auto arrange within the volume of the liquid sample held by the container and a second type of particles which do not auto arrange within the volume of the liquid sample, includes a bottom wall having a recessed portion and a non-recessed portion adjacent the recessed portion. The container thereby defines a first zone situated at a first depth in the volume of the liquid sample and in vertical alignment with the non-recessed portion of the container bottom wall, and a second zone situated at a second depth in the volume of the liquid sample and in vertical alignment with the recessed portion of the container bottom wall. The first type of particles which auto arrange tend to occupy the second zone within the container, and the second type of particles which do not auto arrange tend to occupy the first zone within the container.

As shown in FIG. 8 of the drawings, the container for holding a volume of a liquid sample described above may further include at least one projection, the at least one projection extending upwardly from the non-recessed portion of the container bottom wall and at least partially into the volume of the liquid sample held by the container. The at least one projection is situated on the non-recessed portion of the bottom wall in proximity to the recessed portion of the bottom wall. The at least one projection further acts to separate the first type of particles which auto arrange and which tend to occupy the second zone within the container from the second type of particles which do not auto arrange and tend to occupy the first zone within the container.

Alternatively, and as also shown in FIG. 8 of the drawings, a container formed in accordance with the present invention for holding a volume of a liquid sample and used for separating different types of particles within the volume of the liquid sample, the different types of particles within the volume of the liquid sample held by the container including a first type of particles which auto arrange within the volume of the liquid sample held by the container and a second type of particles which do not auto arrange within the volume of the liquid sample, includes a bottom wall, and a plurality of projections spaced apart from each other over at least a portion of the axial length of the container. The projections extend upwardly from the bottom wall of the container and at least partially into the volume of the liquid sample held thereby. The projections define a first zone and at least a second zone adjacent the first zone. The particles of the first type of particles which auto arrange tend to occupy the first zone within the container, and the particles of the second type of particles which do not auto arrange tend to occupy the at least second zone within the container.

In yet another form of the present invention, and as shown in FIG. 9 of the drawings, a container for holding a volume of a liquid sample and used for separating different types of particles in the volume of the liquid sample, the different types of particles within the volume of the liquid sample held by the container including a first type of particles which exhibit a first dimension, and a second type of particles which exhibit a second dimension which is different from the first dimension exhibited by the particles of the first type of particles, includes a bottom wall, and at least one filter extending upwardly from the bottom wall and at least partially into the volume of the liquid sample held by the container. The at least one filter has a first axial side and a second axial side situated opposite the first axial side. The container defines a first zone within the volume of the liquid sample situated adjacent the first axial side of the at least one filter, and a second zone within the volume of the liquid sample situated adjacent the second axial side of the at least one filter. The at least one filter has a predetermined pore size which allows the particles of the second type of particles of the liquid sample to pass through the at least one filter and into the second zone, whereby the particles of the first type of particles tend to occupy the first zone within the container, and the particles of the second type of particles tend to occupy the second zone within the container.

As can also be seen by FIG. 9 of the drawings, a container formed in accordance with the present invention for holding a volume of a liquid sample and used for separating different types of particles in the volume of the liquid sample, the different types of particles within the volume of the liquid sample held by the container including a first type of particles which exhibit a first dimension, and a second type of particles which exhibit a second dimension which is different from the first dimension exhibited by the particles of the first type of particles, includes a bottom wall, and a plurality of filters spaced apart from each other over at least a portion of the axial length of the container. The filters extend upwardly from the bottom wall and at least partially into the volume of the liquid sample held by the container. The plurality of filters defines at least a first zone within the volume of the liquid sample and a second zone within the volume of the liquid sample. Each filter of the plurality of filters has a pore size which differs from the pore size of the next adjacent filter. At least one of the filters has a pore size which allows particles of the first type of particles to pass therethrough and which does not allow particles of the second type of particles to pass therethrough, whereby the particles of the first type of particles tend to occupy the first zone within the container, and the particles of the second type of particles tend to occupy the second zone within the container.

In an alternative form of the present invention, and as shown in FIG. 4 of the drawings, a container for holding a volume of a liquid sample and used for detecting different types of particles within the volume of the liquid sample, the different types of particles within the volume of the liquid sample held by the container including a first type of particles which auto arrange within the volume of the liquid sample held by the container and a second type of particles which do not auto arrange within the volume of the liquid sample, includes a bottom wall, a first axial end and a second axial end situated opposite the first axial end. The bottom wall has a sloping surface to define the container with a shallower section relatively closer to the first axial end thereof and a deeper section relatively closer to the second axial end thereof, such that a horizontally disposed optical section of the volume of the liquid sample held by the container taken by an optical imaging instrument and having a constant focal plane depth in the volume of the liquid sample, which focal plane depth is selected to be in close proximity to the bottom wall of the container over the shallower section thereof, will detect in a portion of the optical section in alignment with the shallower section of the container particles of the second type of particles which do not auto arrange, and will detect in a portion of the optical section in alignment with the deeper section of the container particles of the first type of particles which auto arrange.

FIGS. 10A and 10B depict another embodiment of a container formed in accordance with the present invention. The container in accordance with this embodiment for holding a volume of a liquid sample and used for detecting different types of particles within the liquid sample, the different types of particles within the volume of the liquid sample held by the container including a first type of particles and a second type of particles, the particles of the first type of particles either auto arrange within the volume of the liquid sample held by the container or have a first dimension, and the particles of the second type of particles either do not auto arrange within the volume of the liquid sample held by the container or have a second dimension which is different from the first dimension of the particles of the first type of particles, includes a bottom wall, and a plurality of spaced apart recesses, projections or particles formed in the bottom wall or situated in proximity to the bottom wall of the container for quality assurance purposes.

In yet another form of the present invention, and as shown in FIG. 6 of the drawings, a container for holding a volume of a liquid sample and used for detecting different types of particles within the liquid sample, the different types of particles within the volume of the liquid sample held by the container including a first type of particles and a second type of particles, the particles of the first type of particles either auto arrange within the volume of the liquid sample held by the container or have a first dimension, and the particles of the second type of particles either do not auto arrange within the volume of the liquid sample held by the container or have a second dimension which is different from the first dimension of the particles of the first type of particles, includes a bottom wall, and a plurality of parallelly disposed and spaced apart plates. The plates extend vertically upwardly from the bottom wall of the container and at least partially into the volume of the liquid sample held by the container, with adjacent plates of the plurality of parallelly disposed plates defining fluid flow channels therebetween. Preferably, the container includes opposite lateral walls, the opposite lateral walls being joined to the bottom wall and extending upwardly therefrom, and a first axial end and a second axial end situated opposite the first axial end. Preferably, at least some of the plates of the plurality of parallelly disposed plates have differing axial lengths which increase from the longitudinal center of the container in symmetrical directions outwardly toward the opposite lateral sides thereof, such as shown in FIG. 6 of the drawings.

Bacteria auto-alignment has been demonstrated with an associated model and experimental data. The auto-alignment model provides insight into the circumstances described previously, and advanced processing, as described below, may be used to quantify bacteria in a liquid sample in the presence of non-bacteria artifacts. Specific examples include the presence of lipids that will tend to float and debris that may settle at a slower rate than formed elements. Based on conceptual models regarding how these elements will behave in urine and how bacteria will behave yields several algorithm approaches that each provides insight into the elements that are seen in the fluid bulk. The algorithm approaches are described to facilitate understanding as to how they can help differentiate bacteria from non-bacteria in the bulk of a urine sample. In addition, an integration model is shown to describe how these disparate algorithm approaches can be combined to yield appropriate bacteria concentration even in the presence of these artifacts.

The auto-arrangement theory described for bacteria is in some degree similar to theories associated with solid state physics crystalline structure models. The key is that within a confined space bacteria will have a surface charge that will interact with other charged bacteria in a repulsive manner (this premise ignores the condition where bacteria become so close that Van der Waals attractive forces dominate the interaction). Since the bacteria are in a confined environment and cannot move infinitely away from each other, they will orient themselves into a condition where the total system is at minimum energy levels, as shown in FIG. 11B. A simple two dimensional model where each bacterium has the same mass, volume, and surface charge is shown in FIG. 12 of the drawings and illustrates that the bacteria will align themselves with equal spacing with respect to each other.

Figure 12:
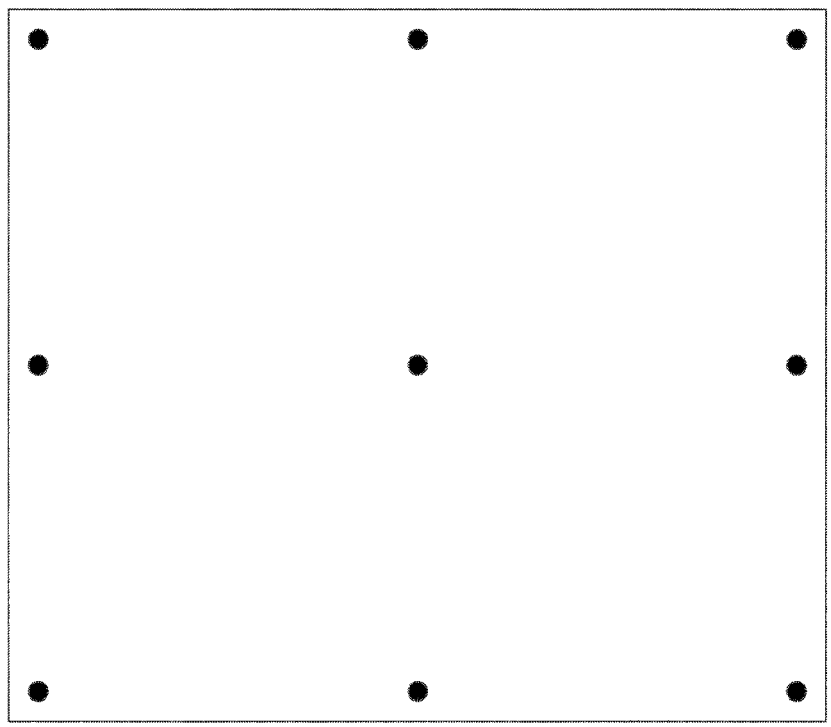
FIG. 12 is a top view of a two dimensional model for bacteria in an auto-arranged state.
Figure 13B:
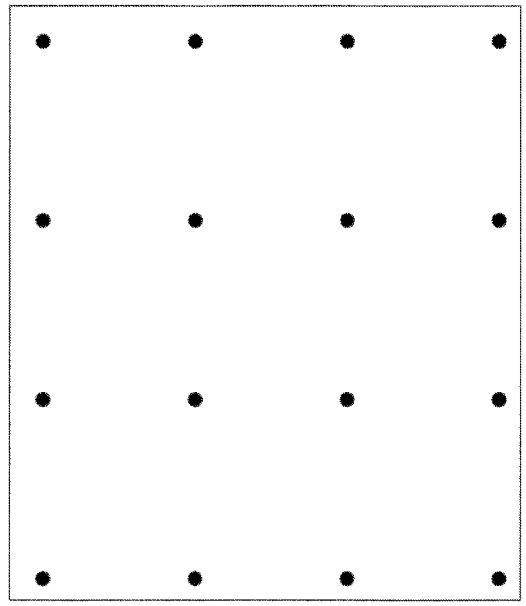
FIG. 13B is a top view of a two dimensional model for bacteria in an auto-arranged state with an increased bacteria concentration than that shown in FIG. 13A.
Figure 13A:
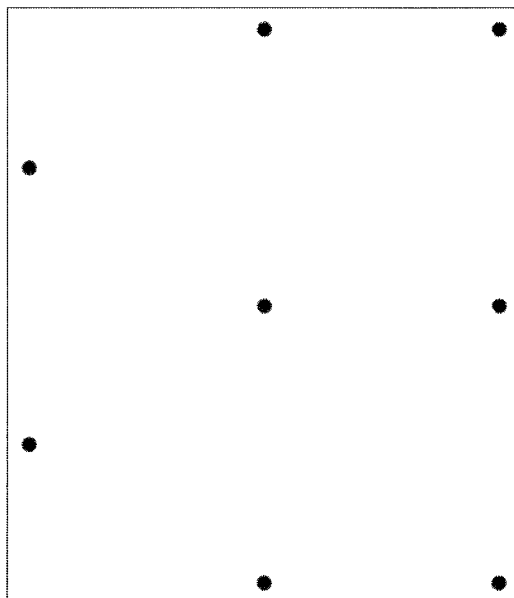
FIG. 13A is a top view of a two dimensional model for bacteria in an auto-arranged state with incomplete bacteria to completely fill the lattice structure.

The diagram in FIG. 12 represents a situation where the number of bacteria elements completely and uniformly fills the lattice-like spaces within the sample container, e.g., a consumable (disposable) device. If there were one-less bacterium in that model, then the resulting model would resemble the graphic shown in FIG. 13A. If, on the other hand, the bacteria count increased from 9 to 16, then the natural spacing would be changed to a smaller distance that is now uniformly consistent to provide that minimum-energy state for the system, as shown in FIG. 13B.

Figure 14:
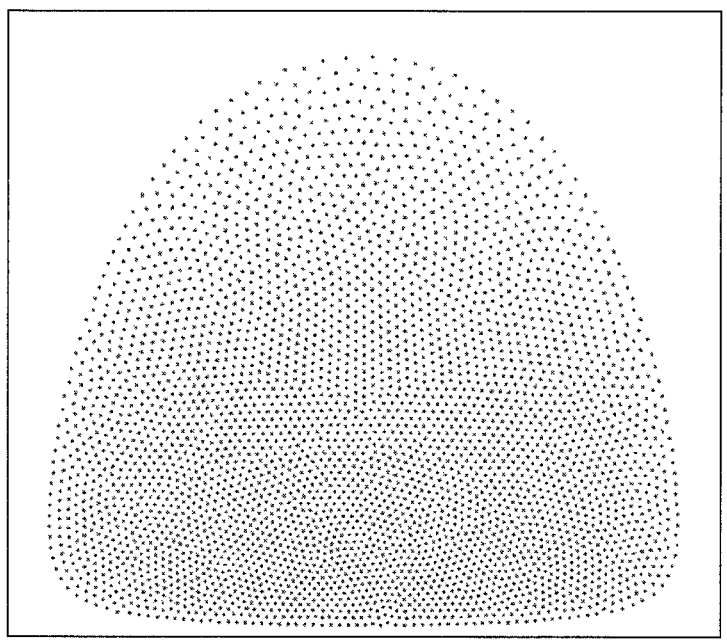
FIG. 14 is a side view of a three dimensional model for bacteria in an auto-arranged state.

When the two dimensional model is evaluated from a vertical profile instead of a top-down view, the effects of gravity and buoyancy come into play. The slightly more complicated model will continue to demonstrate the electrical interaction demonstrated in FIGS. 13A and 13B, but will also incorporate physical characteristics. The difference will be that each horizontal slice taken while moving up or down within the depth of the sample container will be slightly different than the rest. In this condition, the lowest depths will have the highest concentration of bacteria as well as shortest vertical spacing between levels. Moving up in depth will show a reduction in bacteria count as well as an increase in spacing in the depth direction. The top-most horizontal rows will show the widest variation in count and spacing due to incomplete filling of the lattice structure. FIG. 14 shows a side view of the three dimensional model of such structure. The gumdrop shape of the elements show in FIG. 14 is related to the electric charge of the particles as well as the electric charge associated with the consumable sample container edges. The lower concentration of cells in the upper area provides less force and the walls of the sample container push the cells towards the middle.

Imaging within the bulk of a urine sample has shown that bacteria follow the simple models described above. Evaluating bacteria in the fluid bulk provides an easy way to separate bacteria from formed elements, such as red blood cells (RBC), white blood cells (WBC), epithelial cells, casts, and crystals, by allowing gravity to hasten settling of the formed elements while the bacteria remains suspended. Some artifactual elements in the urine sample do not show the standard formed element settling profile of approximately 100 μm of settling per minute. The most common of those elements are lipids and debris.

Figure 15:
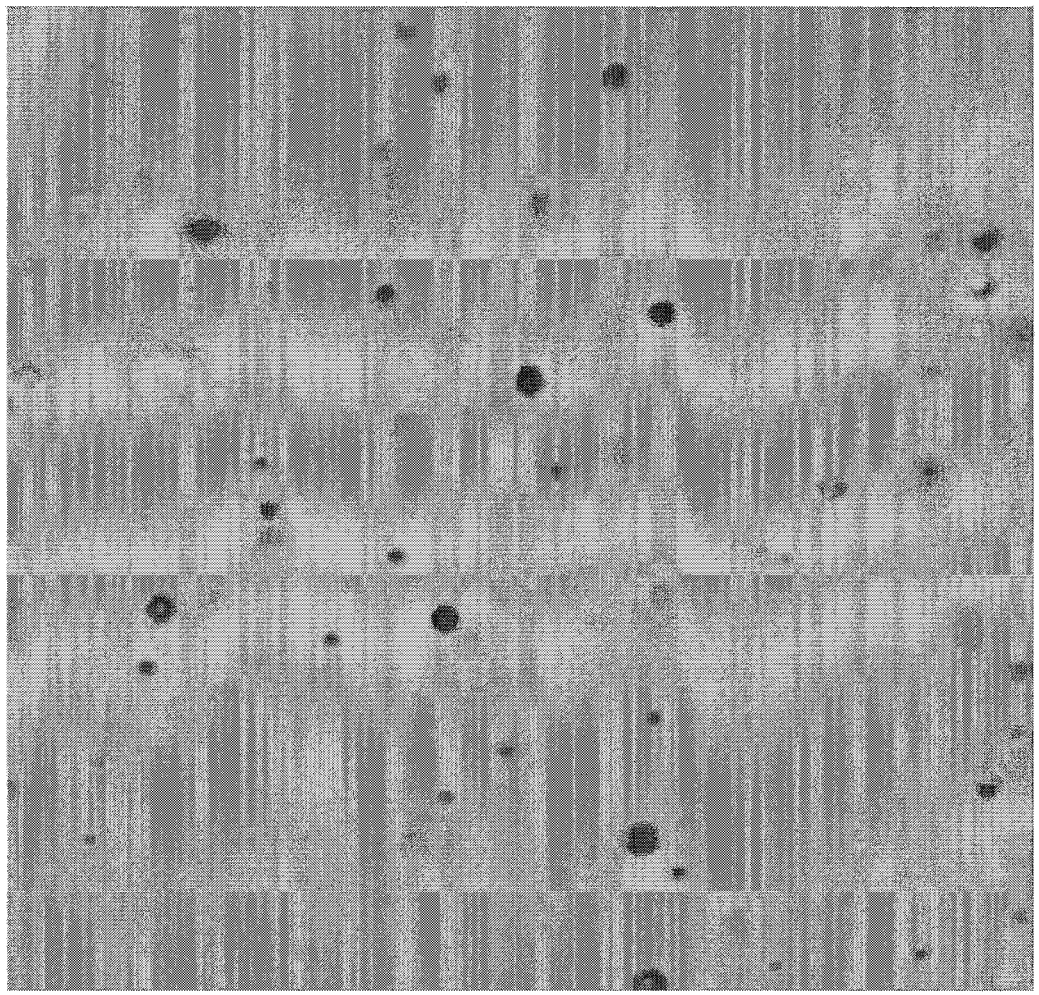
FIG. 15 is an inverted brightfield microscopy photographic image, showing a representative sample containing varying sized lipids without bacteria in a fluid bulk.

Evaluation of lipids suggests that they will not have the same electrical surface charge as bacteria and will not interact electromagnetically with the bacteria. The density of lipids will be lower than the urine sample and the lipids will be prone to float to the top of the sample. Filling the sample container will randomly distribute the lipids throughout the fluid and then with time the lipids will rise. The lipids will also vary significantly in size, from about the size of bacteria to much larger. When the lipid concentration is high, there will likely be significant levels of lipids (including those that are similar in size to bacteria) in the region where one might choose to evaluate the sample for bacteria (such as 650 µm from the sample container bottom in the deepest zone). The interaction between lipids and bacteria will then have the highest level of interaction at the top-most depths of the sample container where bacteria will be found. The image in FIG. 15 shows a representative sample containing lipids without bacteria in the fluid bulk.

Figure 16:
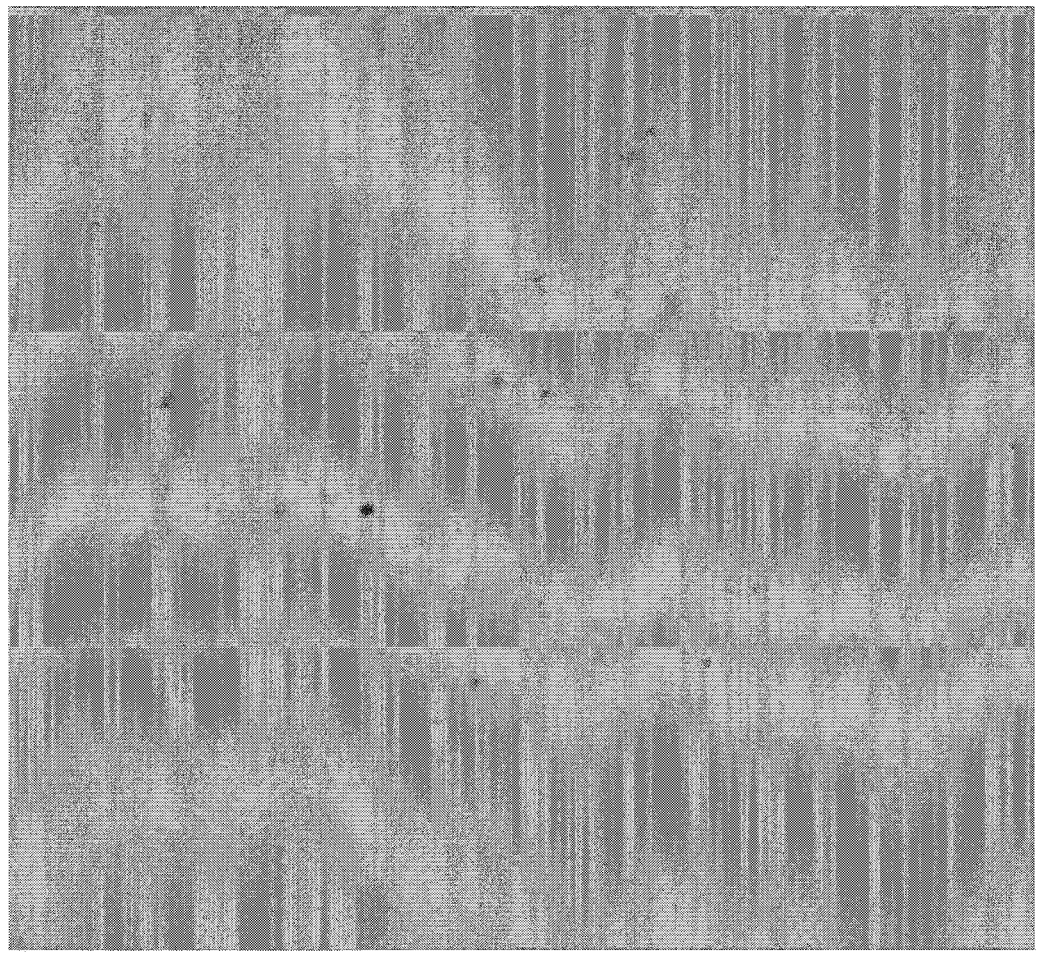
FIG. 16 is an inverted brightfield microscopy photographic image, showing a representative sample containing debris without bacteria in a fluid bulk.

Debris will, similarly to lipids, have widely varying sizes, though debris will settle due to a higher density. The range of shapes and small sizes of debris can result in very long settling times, as buoyancy and gravity can have similar, but opposite in direction, force magnitudes. This will result in a mostly randomly distributed debris profile (the debris will also not be charged) that has the potential to fall either faster or slower than bacteria (though bacteria will be governed by electrical forces, as well, that will dictate the final resting position). In the end, debris will either remain randomly distributed, settle, or float. FIG. 16 shows a representative sample containing debris without bacteria in the fluid bulk.

Figure 17A:
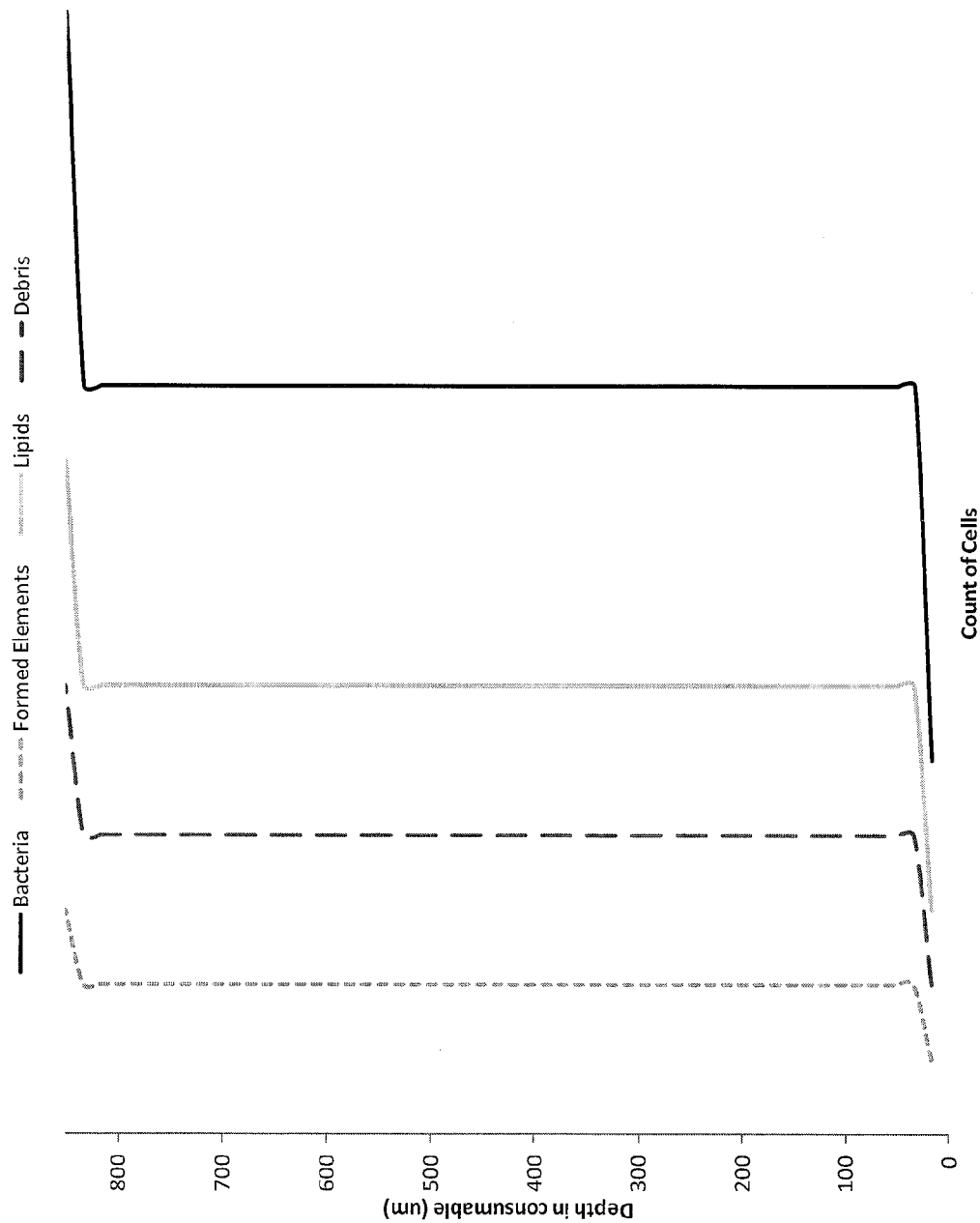
FIG. 17A is a theoretical histogram model overlay, showing each of four particle types (bacteria, formed elements, lipids and debris) present in a sample container at a time when the container is just filled with a urine sample, the ordinate representing the depth in the sample container, in microns ($\mu$m), and the abscissa representing cell count for the four particles.
Figure 17B:
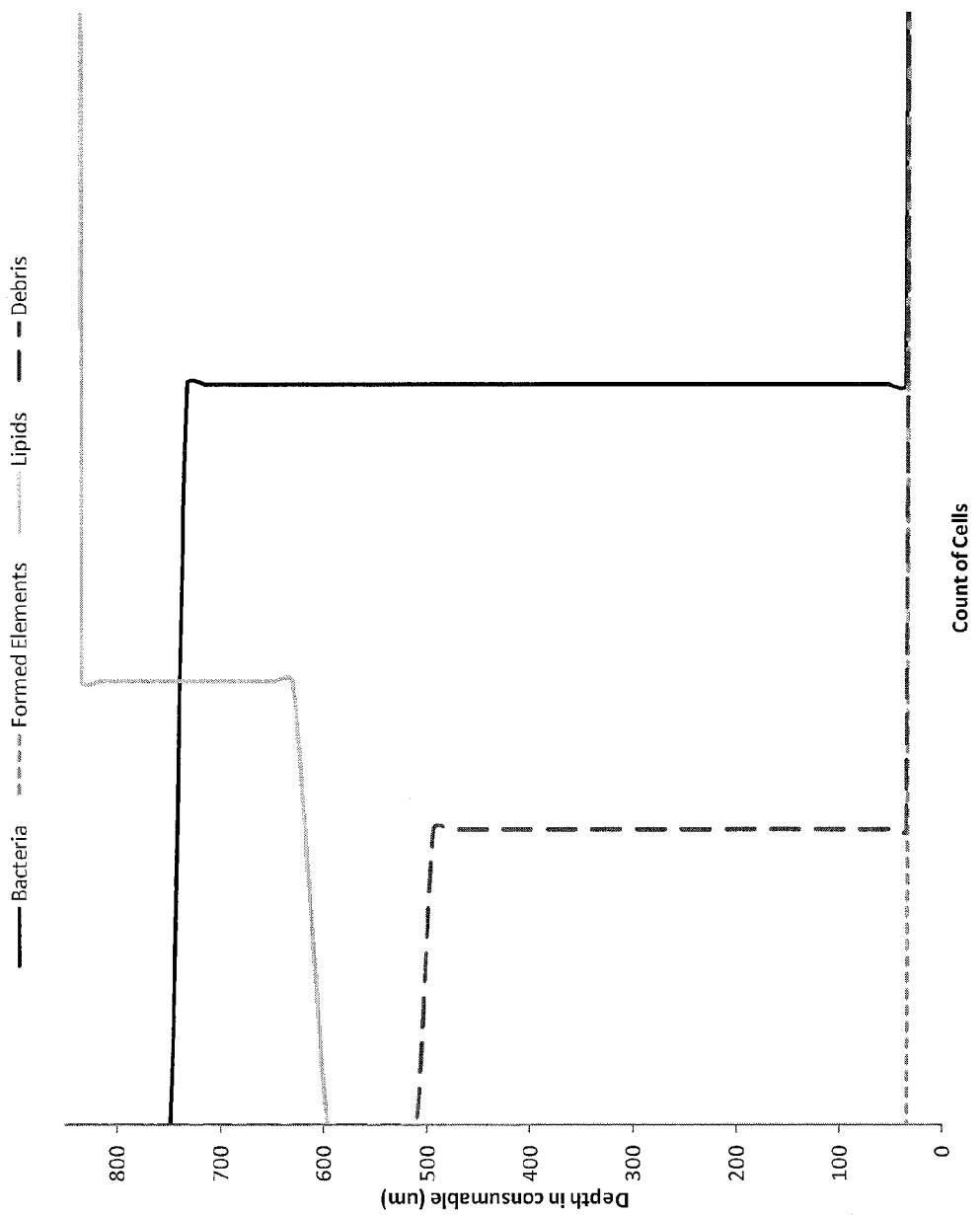
FIG. 17B is a theoretical histogram model overlay, showing each of four particle types (bacteria, formed elements, lipids and debris) present in a sample container at some elapsed time after the container is filled with a urine sample and after some settling of particles has occurred, the ordinate representing the depth in the sample container, in microns ($\mu$m), and the abscissa representing cell count for the four particles.

Lipids and bacteria will each have a distinct distribution through the fluid depth depending on if they float (lipids), remain randomly distributed (debris), or sink (debris). The distribution through the fluid depth will then generate different information from bacteria which will follow the auto-alignment model. Evaluation of different depths as well as different points in time will provide the necessary data to differentiate bacteria from these interfering agents. FIGS. 17A and 17B show an overlay of theoretical histograms representing each of the four particle types at time zero (when the sample container is just filled) (FIG. 17A) and after some settling has occurred (FIG. 17B) to demonstrate the potential depth performance. Time and depth data will separate the different elements.

Figure 18A:
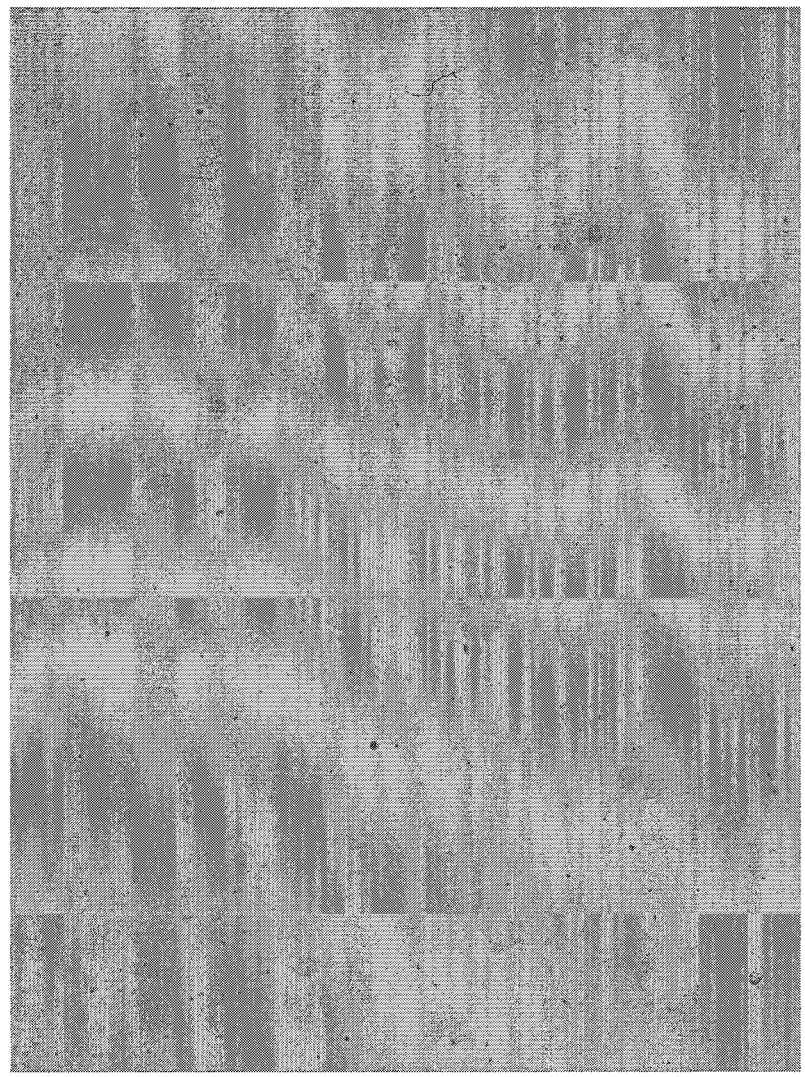
FIG. 18A is a brightfield microscopy raw image of bacteria in a fluid bulk, prior to the image being thresholded.
Figure 18B:
FIG. 18B is the image shown in FIG. 18A after the image is thresholded, for an object count analysis in accordance with the present invention.

A first "object count" algorithm approach in accordance with the present invention may be used to help differentiate bacteria from non-bacteria in a urine sample and is described below. Consider the presence of elements in the bacteria zone. It is fairly easy to visualize small dots (representing bacteria or other small artifact elements) distributed within an image. Since the measurement is captured in the fluid bulk, there is no in-focus plane and each image will have in-focus and out-of-focus elements at each portion of the image (independent of off-axis angle). A straight forward measurement can be made by thresholding the image and identifying the objects from the background (e.g., turning each pixel into a grayscale value and then choosing any pixel above a certain threshold value to be white while all other pixels are black). Counting all of the individual white areas (each connected white pixel will be considered as one element) will yield the object count. An example raw image and associated thresholded image are shown in FIGS. 18A and 18B, respectively.

The object count will provide a quantitative value that can be used to determine concentration of particles within the image. For a pure bacteria sample, this count will directly correlate with the bacteria concentration. When other particles exist in the same plane as the bacteria, then the object count will be higher than the bacteria count. For a sample with small particles and no bacteria, the concern would be that a bacteria concentration would yield from the analysis (when there should be none reported). From FIG. 17B, it may be seen that, if the sample is allowed to settle for an appropriate period, then there may be a "sweet spot" zone where that concentration is only bacteria.

A second density algorithm approach in accordance with the present invention may be used to help differentiate bacteria from non-bacteria in a urine sample and is described below. The density analysis follows directly from the object count analysis. The difference is that the density evaluation determines the ratio of thresholded elements (white pixels) to a background containing all black pixels (see FIG. 18B). This analysis takes into consideration the size of the bacteria as well as the count. The image in FIG. 18A may be used to determine density by performing post-processing tools such as thresholding to isolate the particles from the background, as shown in FIG. 18B. Density has the potential to provide a measure of concentration. Knowing that debris and lipids will have varied sizes, the impact of having those present in the image will increase the density without increasing the object count. Comparing the quantified values from these two measurements could start to identify if non-bacteria elements are part of the thresholded image.

Figures 19A, 19B:
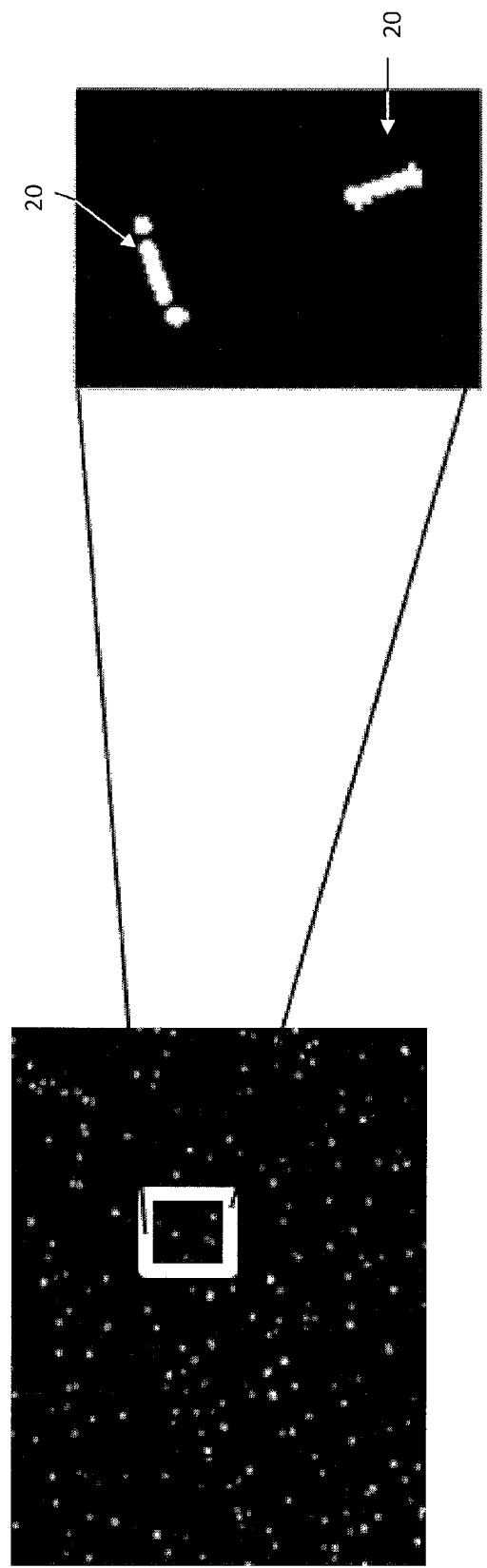
FIG. 19A is another example of a thresholded image similar to that shown in FIG. 18B for determining pixel spacing in accordance with the present invention.
FIG. 19B is an enlarged portion of the thresholded image shown in FIG. 19A with post-processed lines indicating spacing to nearest neighbor.

A third "pixel spacing" algorithm approach in accordance with the present invention may be used to help differentiate bacteria from non-bacteria in a urine sample and is described below. Pixel spacing is intended to determine the average distance between particles in the fluid bulk. If the auto-alignment theory is followed by the particles, then the spacing between particles will be smaller as the concentration increases. The standard deviation of the distances should also indicate if the auto-alignment process has occurred or if there are other non-bacteria particles in the image that do not align. The general approach is to find the thresholded image similar to that from FIG. 18B and then calculate the shortest Euclidean distances between particles (i.e., nearest neighbors). Pixel spacing is then determined by calculating the average and standard deviation of these distances, as represented in FIGS. 19A and 19B. As shown in FIG. 19B, the threshold image may be modified to add a post processing line 20 between neighboring bacteria, the length of which is indicative of the spacing between a bacterium and its nearest neighbor bacterium.

A theoretical model can be developed to describe the pixel spacing based on the size and charge of bacteria, the dimensions of the sample container, and the time allowed to align. This model can be confirmed through empirical data. The impact of non-debris is that there will be disruptions in the pixel spacing model, artificially shrinking the average spacing and expanding the standard deviation.

Figures 20A, 20B:
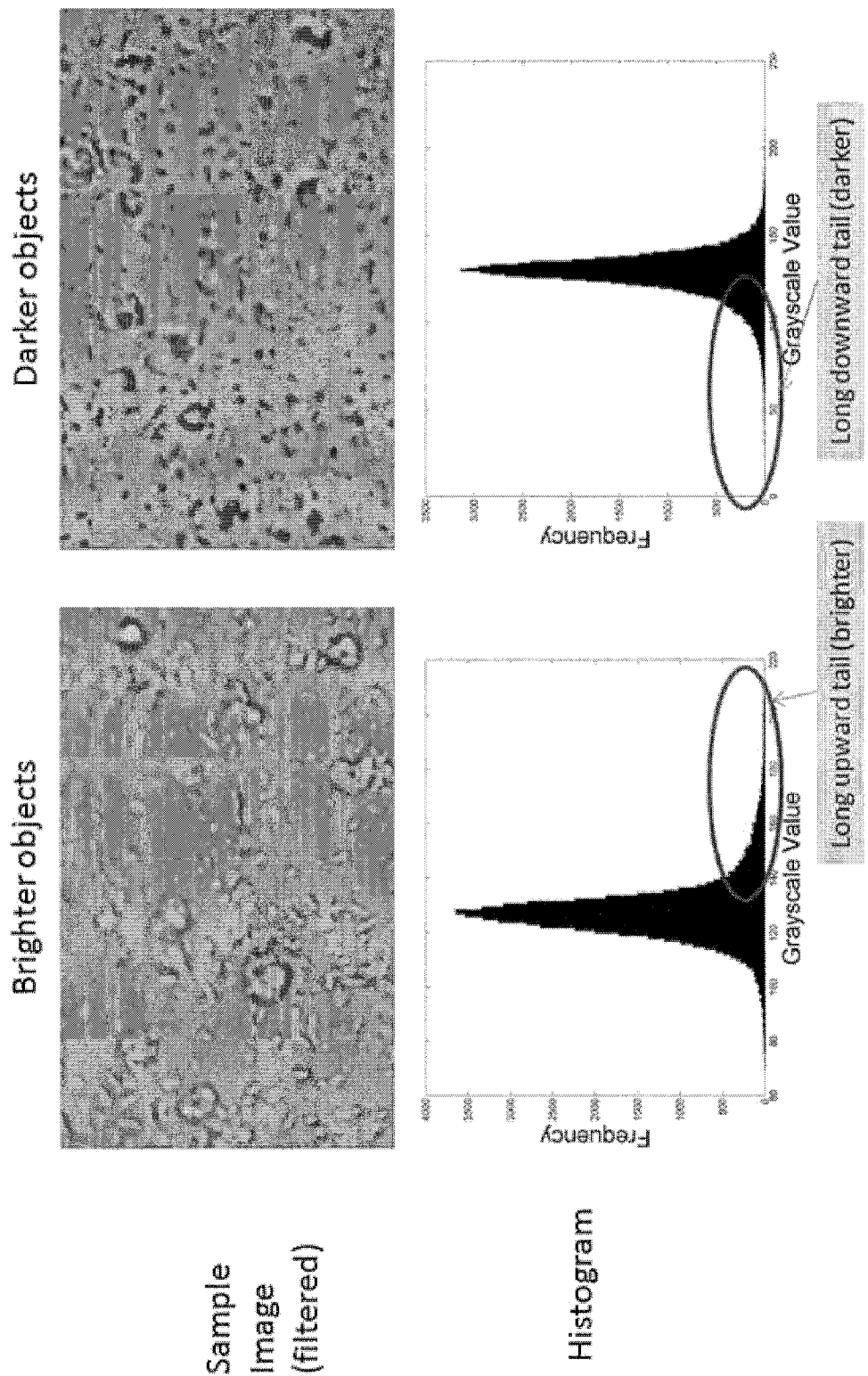
FIG. 20A is a photographic image of a urine sample (for brighter objects) and its associated histogram, with frequency as the ordinate and grayscale value as the abscissa, illustrating skewness as a measurement to determine the distribution of bacteria through a fluid bulk in accordance with a method of the present invention.
FIG. 20B is another photographic image of a urine sample (for darker objects) and its associated histogram, with frequency as the ordinate and grayscale value as the abscissa, illustrating skewness as a measurement to determine the distribution of bacteria through a fluid bulk in accordance with a method of the present invention.

A fourth "skewness" algorithm approach in accordance with the present invention may be used to help differentiate bacteria from non-bacteria in a urine sample and is described below. Skewness is a measurement of the normality of a data set. A positive skew indicates that the data has an extended tail to the right, while a negative skew indicates an extended tail to the left, as shown in FIGS. 20A and 20B. Skewness can be calculated for any image, and if the distribution of grayscale values follows a Gaussian curve, then it will have a near-zero skewness. If there is an excessive tail, then the skewness value will demonstrate that.

Since bacteria will be normally distributed through the fluid bulk, the skewness is expected to be near zero. Even with an off-axis image that is intended to have an in-focus band and out-of-focus bands when located at the sample container bottom (for settled objects), images in the fluid bulk with randomly distributed particles will have a near-zero skewness. As particles settle, they will demonstrate skewness near the bottom of the sample container and will not be seen higher in the bulk. Similarly, objects that float will demonstrate skewness in the upper regions and will not be seen lower in the sample container.

The four algorithm approaches of the present invention described above each have strengths and weaknesses when bacteria are present with interfering artifacts such as lipids and debris. Evaluation of the output of each approach in an integrated manner will provide additional information to help quantify bacteria and determine the potential impact of that value by artifacts. Consider the theoretical model shown in FIG. 17A. Initially in the sample, all of the particles are randomly distributed through the fluid bulk, as shown in FIG. 17A. As time passes, dense objects will settle at some rate, low-density particles will float at some rate, and bacteria will settle into the auto-aligned grid. FIG. 17B demonstrates that there is a time and space within the sample container where complete separation of bacteria from non-bacteria is possible.

Figure 21:
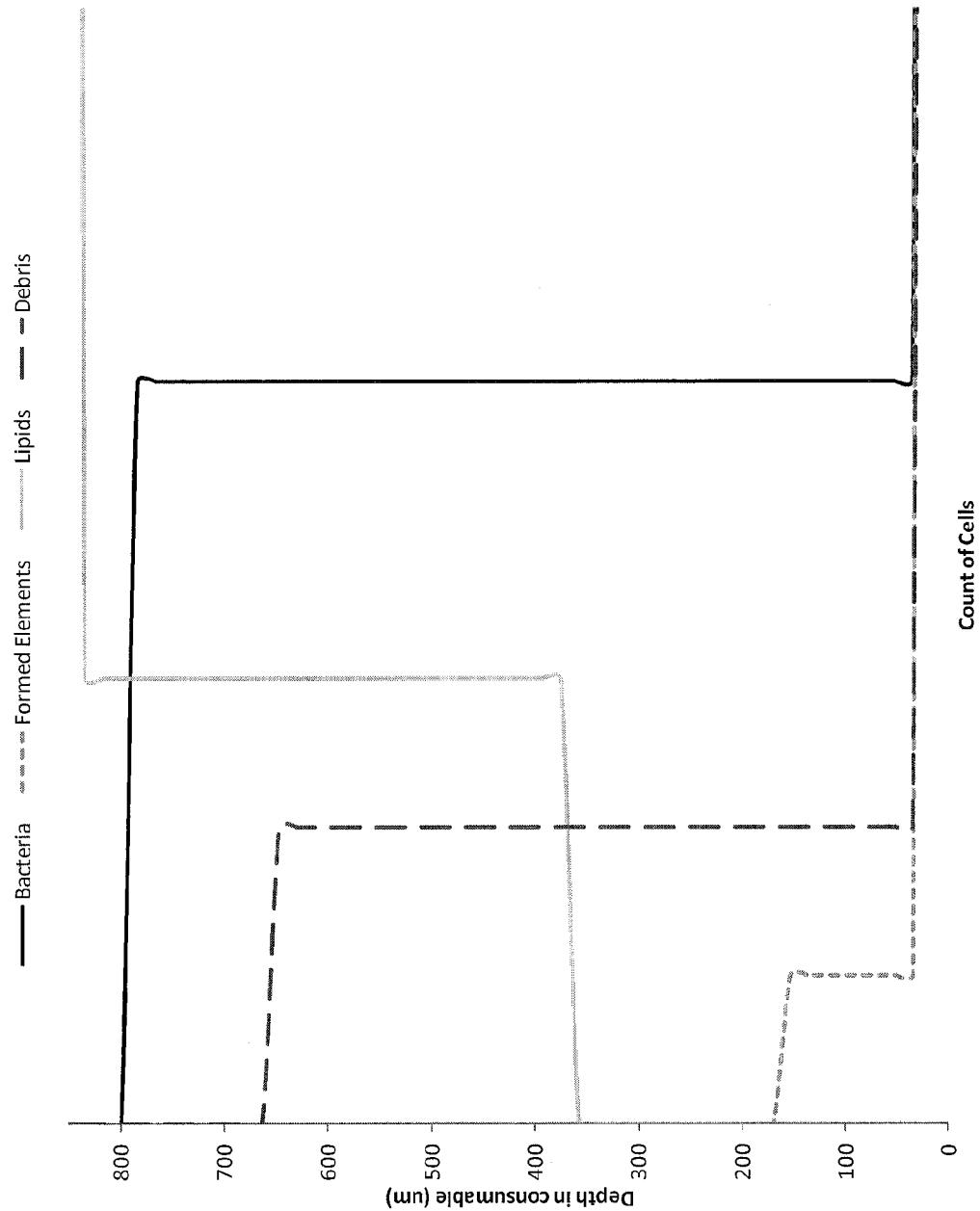
FIG. 21 is a theoretical histogram model overlay, similar to that shown in FIGS. 17A and 17B, showing each of four particle types (bacteria, formed elements, lipids and debris) present in a sample container at a time between when the container is just filled with a urine sample (see FIG. 17A) and prior to the elapsed time (see FIG. 17B), and illustrating where particle separation has begun but is not complete, the ordinate representing the depth in the sample container, in microns (μm), and the abscissa representing cell count for the four particles.

A third time point between the "fill time" histogram shown in FIG. 17A and the "settled time" histogram shown in FIG. 17B is depicted in the histogram shown in FIG. 21, where particle separation has begun but is not complete.

It is clear from FIGS. 17 and 21 that there are regions where bacteria will overlap with a subset of contaminants instead of all three types described. This vertical separation can be used to determine the impact from each of the four algorithm approaches of the present invention with respect to elements at each depth. By performing a vertical scan through the sample container, the impact of the elements at each level in depth can be compared with pure bacteria titrations to determine the concentration. By evaluating at several depths, the different artifact elements can be extracted from the data. In addition, performing the vertical scan at different times after filling the sample container will also provide temporal separation that will indicate settling/floating rates. All of these inputs can be integrated to determine concentration and rate potential for contamination impacting the concentration value.

Figure 22A:
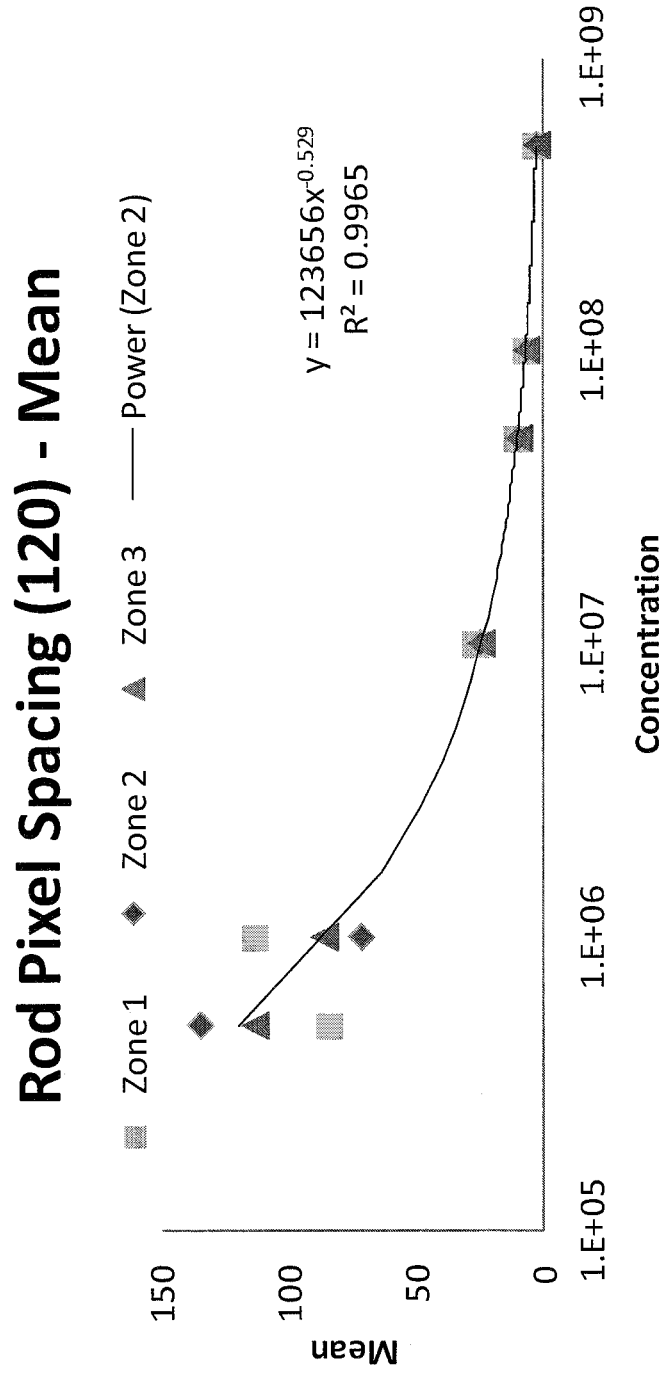
FIG. 22A is a graph of a calibration curve for the titration of bacteria (rods) with pixel spacing logic in accordance with the present invention performed at each of three depths (200, 400, and 600 microns) within a container holding a urine sample, where the ordinate represents the pixel spacing mean and the abscissa represents the concentration of bacteria within the sample.
Figure 22B:
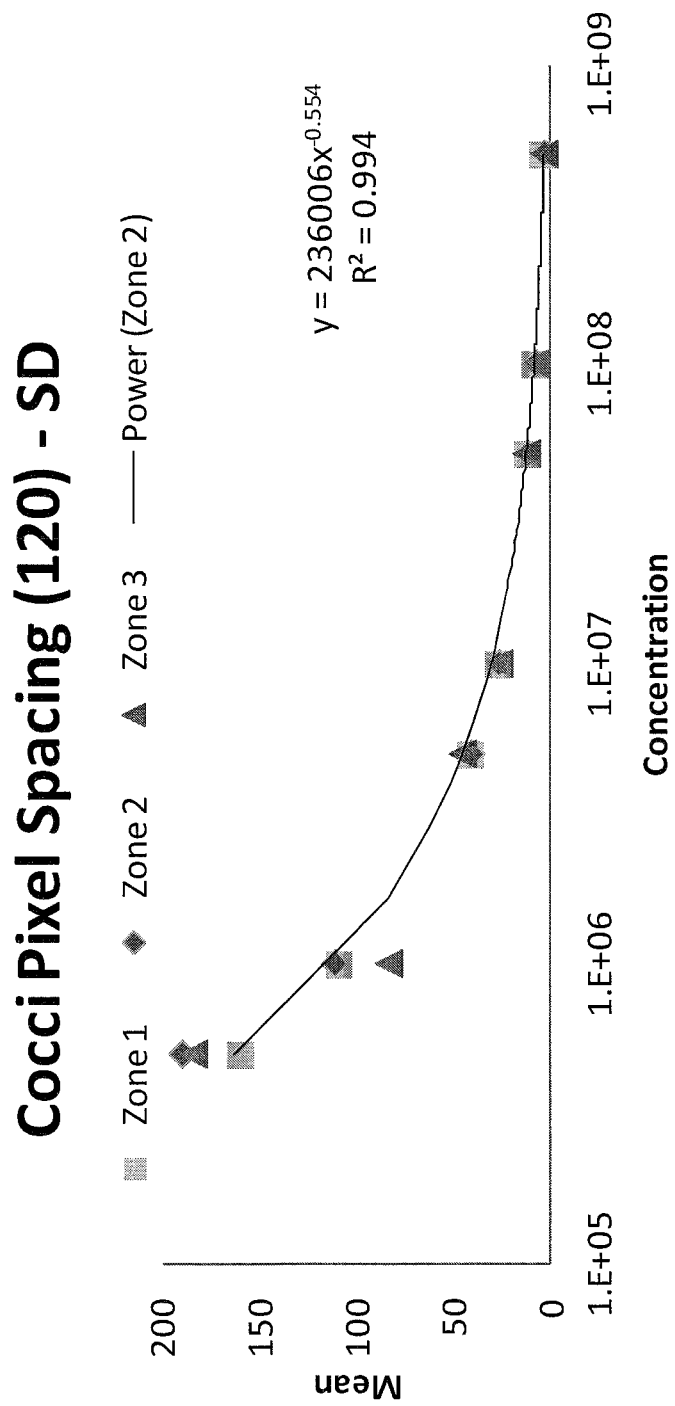
FIG. 22B is a graph of a calibration curve for the titration of bacteria (cocci) with pixel spacing logic in accordance with the present invention performed at each of three depths (200, 400, and 600 microns) within a container holding a urine sample, where the ordinate represents the standard deviation of pixel spacing and the abscissa represents the concentration of bacteria within the sample.

Consider the data shown in FIGS. 22A (rods) and 22B (cocci), where a bacteria titration was evaluated using the standard bacteria scan in a sample container, e.g., a consumable (disposable) device, such as shown in FIGS. 24-28 of the drawings (data shown from all three zones) and post-processing with "pixel spacing" logic, as described previously. The curves for both mean and standard deviation are shown in FIGS. 22A and 22B, respectively, with a representative well-fit power series curve for each. Since this particular sample container has bacteria zone depths that drop off with each zone, the depth of analysis for each zone is different (e.g., 600, 400, and 200 µm from the container bottom). The curves overlay for each zone because the sample is pure bacteria and there are no interfering artifacts present in the sample to affect the logic. There is a potential time-dependent curve that could be implemented as the auto-arrangement process progresses and the system evaluates at different depths (potentially the reason for the variation noted at $10^6$/ml concentration).

Given the calibration curves shown in FIGS. 22A and 22B, the bacteria concentration may be based on a "pixel spacing" mean calculation. If there were no interfering factors, then the calculation would be complete. If potential interfering factors are present, then integration of similar curves from the remaining algorithms described previously, as well as a re-analysis at a follow-on time, provide more information to achieve increased accuracy.

Figure 23A:
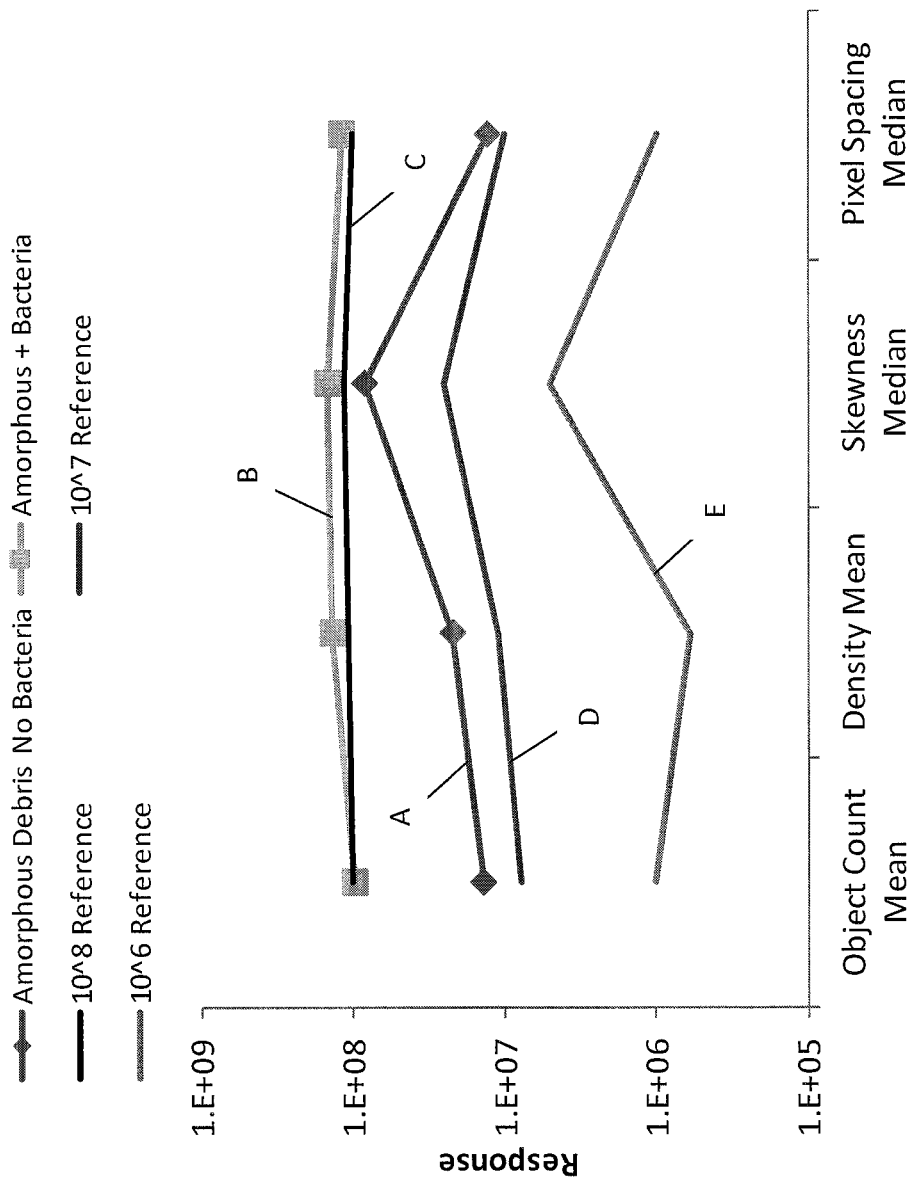
FIG. 23A is a graph illustrating the integration of four algorithm approaches in accordance with the present invention used to differentiate bacteria from non-bacteria in a urine sample, where the ordinate represents the response and the abscissa represents the object count mean, the density mean, the skewness median and the pixel spacing median, for a bacteria concentration with amorphous debris spiked with bacteria.
Figure 23B:
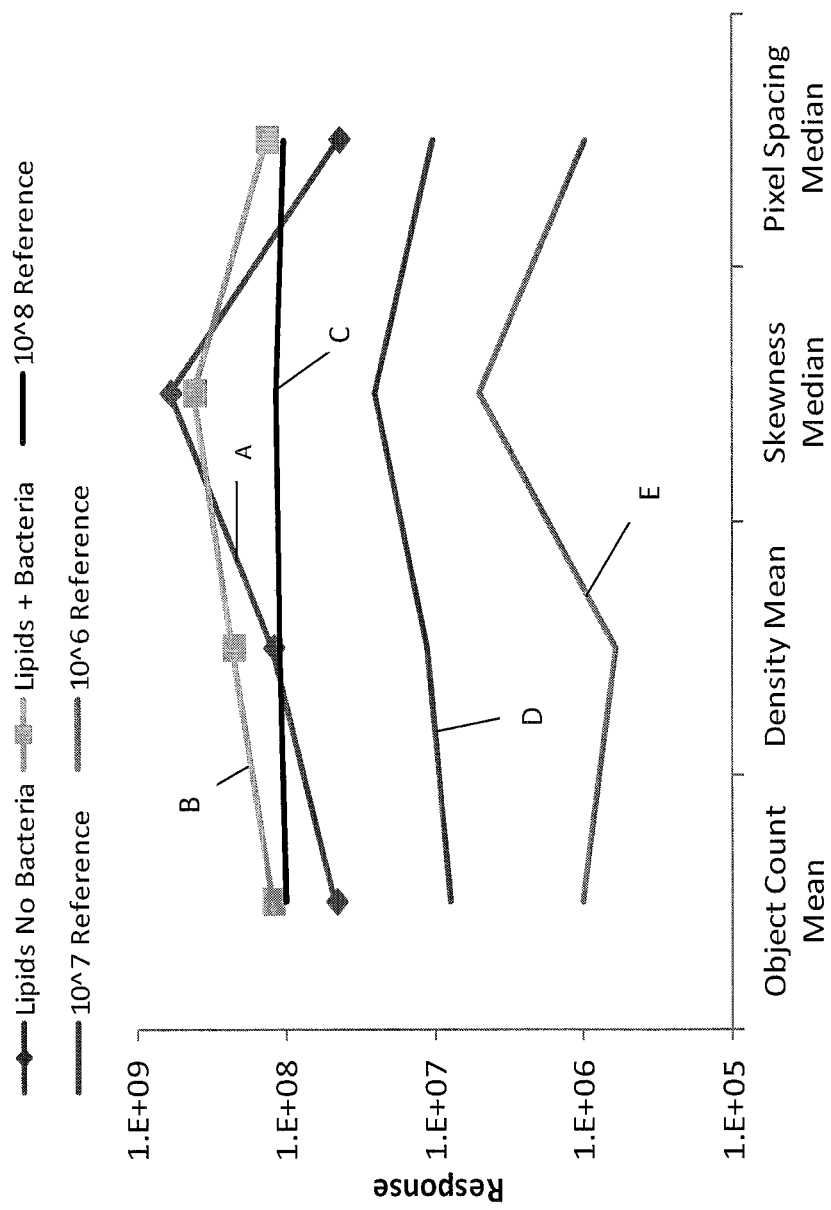
FIG. 23B is a graph illustrating the integration of four algorithm approaches in accordance with the present invention used to differentiate bacteria from non-bacteria in a urine sample, where the ordinate represents the response and the abscissa represents the object count mean, the density mean, the skewness median and the pixel spacing median, for a bacteria concentration with lipids spiked with bacteria.
Figure 24:
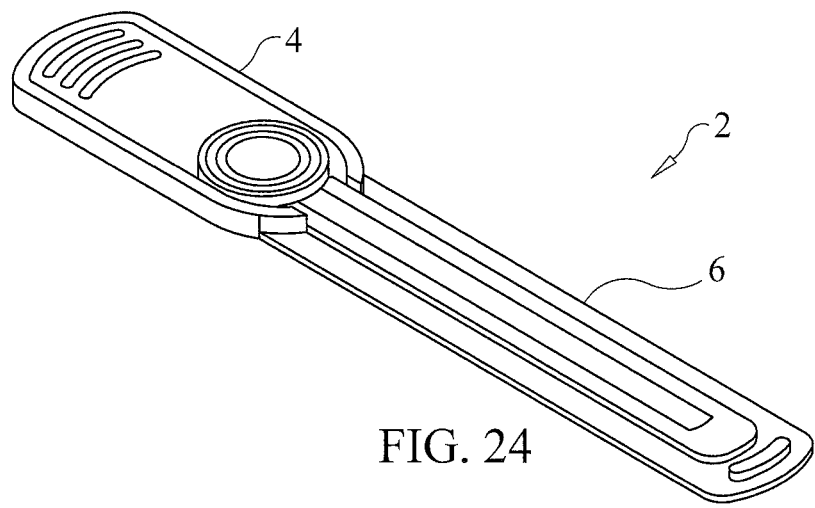
FIG. 24 is a top perspective view of a tenth embodiment of a consumable container formed in accordance with the present invention to aid in carrying out the method of the present invention for detecting bacteria and determining the concentration thereof in a liquid sample.
Figure 25:
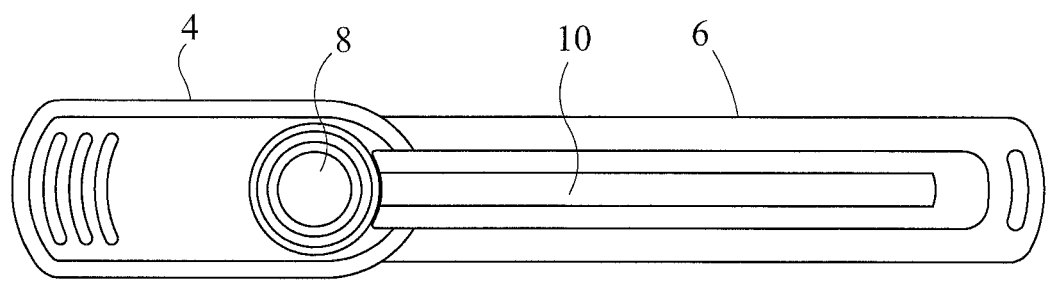
FIG. 25 is a top plan view of the tenth embodiment of the consumable container formed in accordance with the present invention and shown in FIG. 24.
Figure 26:
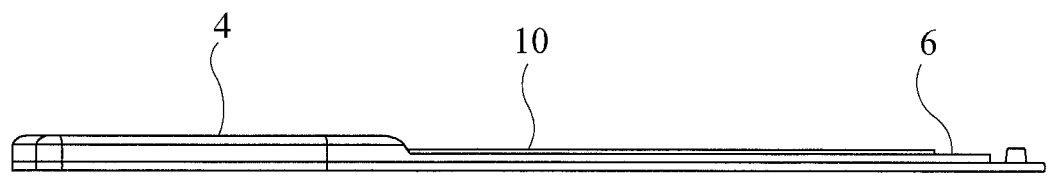
FIG. 26 is a side view of the tenth embodiment of the consumable container formed in accordance with the present invention and shown in FIG. 24.
Figure 27:
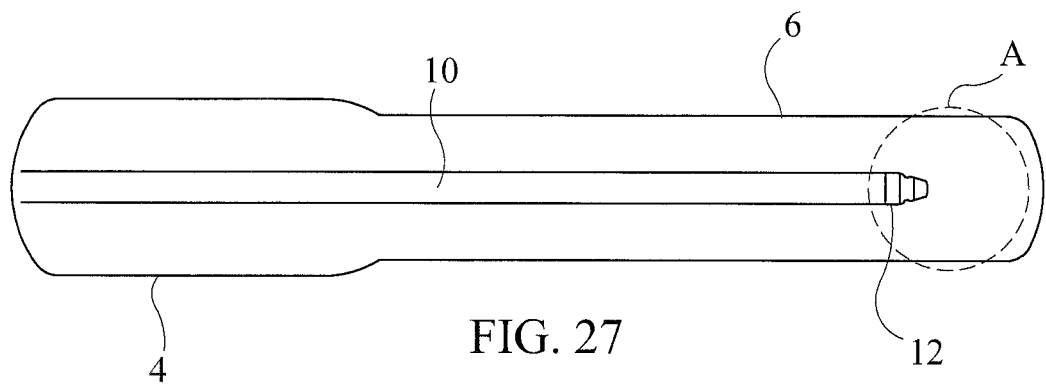
FIG. 27 is a bottom plan view of the tenth embodiment of the consumable container formed in accordance with the present invention and shown in FIG. 24.
Figure 28:
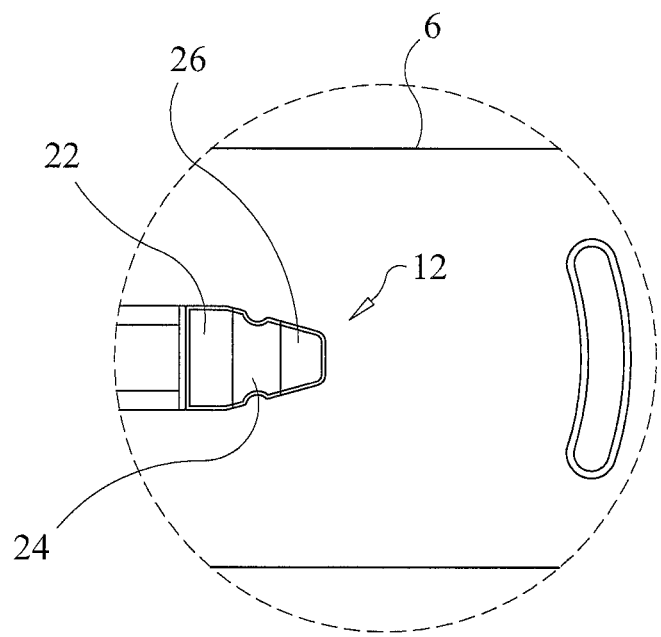
FIG. 28 is an enlarged bottom plan view of the tenth embodiment of the consumable container of the present invention shown within the broken line circle labeled with reference letter A in FIG. 27.

An instructional method to visualize integration of the four algorithms together (for this example assumes that there is no temporal impact) is shown in FIGS. 23A and 23B. The method shows reference curves for each of the algorithm outputs at three concentrations of pure bacteria. The dark line A with markers represents the native sample that contained no bacteria. The gray line B with markers represents the native sample spiked with $10^8$ cocci/ml. In the case of both lipids and bacteria, the native sample shows significant differences from the reference curves C, D and E. When spiked with $10^8$ cocci/ml, curve B shows greater similarity to the corresponding reference curve C. To add more clarity, evaluation of object count and pixel spacing shows that, when both are very close to the natural reference, then they are good representations of the bacteria concentration. Object density and skewness show the impact of the artifact in conjunction with spiked bacteria. This representation shows how an integrated model could be created from this type of data.

A quantitative model can be created from preferably six reference data points: time from fill, vertical position in the bacteria zone, object count, pixel spacing, object density, and skewness. It should be noted that it is possible to evaluate mean, median, and standard deviation for each of the four algorithms. For each time and vertical position (bacteria zone dependent), a calibration curve may be created for a pure bacteria titration (generally expected to be a power-series fit) for each of mean, median, and standard deviation. These twelve values will be the algorithm logic inputs from a measurement. The fit model for the appropriate depth and time point will then be used to evaluate concentration estimates from each of the twelve algorithms based on the sample response. Integration of the twelve algorithms can be performed by an expert system incorporating fuzzy logic curves to characterize if a sample contains bacteria or not. Samples that are determined to have bacteria will then predict concentration from the reference curves. Actual concentration may require a second expert fuzzy logic system, especially for low concentration bacteria where artifacts can have a larger impact. It is possible that using this approach and considering time from fill, the lower limit of detection can be reduced below $10^6$ cocci/ml.

As is evident from the foregoing description, the method of the present invention can evaluate bacteria in bulk fluid and uses the characteristics of the bacteria as a means to differentiate bacteria from non-bacteria "debris". It is a highly sensitive and selective method for detecting bacteria, especially in a urine medium, and may be used to determine the concentration of the bacteria in the liquid sample. Furthermore, in accordance with one form of the method of the present invention, the average spacing between bacterium may be measured to estimate the bacteria concentration, instead of attempting to count bacteria.

The various forms of the container of the present invention shown in FIGS. 2-10 of the drawings help carry out the method of detecting and quantifying the bacteria in a fluid sample, and separating the bacteria from non-bacteria "debris".

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for detecting bacteria and determining the concentration thereof in a liquid sample, which comprises the steps of:
    taking at least one optical section through a volume of the liquid sample with a fluid imaging system having a camera at a predetermined field of view and at a predetermined focal plane depth or angle in the volume and after a predetermined time has elapsed to allow bacteria in the liquid sample to auto arrange in a uniform distribution;
    counting the number of bacteria present within the at least one optical section with the fluid imaging system;
    calculating the number of optical sections into which the volume of the liquid sample may be divided with the fluid imaging system thereby determining a total number of possible optical sections;
    multiplying the number of bacteria present in the at least one optical section by the total number of possible optical sections with the fluid imaging system thereby determining at least an approximation of the total number of bacteria within the volume of the liquid sample; and
    determining the concentration of bacteria within the liquid sample based on the at least approximation of the total number of bacteria within the volume of the liquid sample by the fluid imaging system.

2. A method for detecting bacteria and determining the concentration thereof in a liquid sample as defined by claim 1, wherein the predetermined time allowed for bacteria in the liquid sample to auto arrange is between about three minutes and about ninety minutes.

3. A method for detecting bacteria and determining the concentration thereof in a liquid sample as defined by claim 1, wherein the predetermined time allowed for bacteria in the liquid sample to auto arrange is between about three minutes and about 10 minutes.

4. A method for detecting bacteria and determining the concentration thereof in a liquid sample as defined by claim 1, wherein the at least one optical section taken through the volume of the liquid sample has a focal plane angle of about zero (0) degrees to about ninety (90) degrees relative to a vertical plane through the volume.

5. A method for detecting bacteria and determining the concentration thereof in a liquid sample as defined by claim 1, wherein the at least one optical section taken through the volume of the liquid sample has a focal plane angle of about zero degrees relative to a vertical plane through the volume.

6. A method for detecting bacteria and determining the concentration thereof in a liquid sample as defined by claim 1, wherein the at least one optical section taken through the volume of the liquid sample has a focal plane angle of about ninety degrees relative to a vertical plane through the volume.

7. A method for detecting bacteria and determining the concentration thereof in a liquid sample as defined by claim 6, wherein the optical section has a focal plane depth of at least one of about 100 microns, about 200 microns, about 400 microns, about 600 microns, about 800 microns, about 1,000 microns and about 1,200 microns above the bottom of the volume of the liquid sample.

8. A method for detecting bacteria and determining the concentration thereof in a liquid sample, which comprises the steps of:
    taking a plurality of optical sections through a volume of the liquid sample with a fluid imaging system having a camera at a predetermined field of view and at one or more predetermined focal plane depths or angles in the volume and after a predetermined time has elapsed to allow bacteria in the liquid sample to auto arrange in a uniform distribution;
    counting the number of bacteria present within each optical section of the plurality of optical sections with the fluid imaging system;
    calculating an average of the number of bacteria present by dividing the total number of bacteria present in the plurality of optical sections by the number of optical sections taken through the volume of the liquid sample with the fluid imaging system thereby determining an average number of bacteria present within the optical sections of the plurality of optical sections;
    calculating the number of optical sections into which the volume of liquid sample may be divided with the fluid imaging system thereby determining a total number of possible optical sections;
    multiplying the average number of bacteria present in the optical sections of the plurality of optical sections by the total number of possible optical sections with the fluid imaging system thereby determining at least an approximation of the total number of bacteria within the volume of the liquid sample; and
    determining the concentration of bacteria within the liquid sample based on the at least approximation of the total number of bacteria within the volume of the liquid sample by the fluid imaging system.

9. A method for detecting bacteria and determining the concentration thereof in a liquid sample, which comprises the steps of:
    taking at least one optical section through a volume of the liquid sample with a fluid imaging system having a camera at a predetermined field of view and at a predetermined focal plane depth or angle in the volume and after a predetermined time has elapsed to allow bacteria in the liquid sample to auto arrange in a uniform distribution;
    determining the average spacing between bacteria present within the at least one optical section with the fluid imaging system thereby determining the average bacteria spacing;
    calculating the three dimensional area occupied by the volume of the liquid sample with the fluid imaging system thereby determining a three dimensional volumetric area;
    dividing the three dimensional volumetric area by the average spacing between bacteria with the fluid imaging system thereby determining at least an approximation of the total number of bacteria within the volume of the liquid sample; and
    determining the concentration of bacteria within the liquid sample based on the at least approximation of the total number of bacteria within the volume of the liquid sample by the fluid imaging system.

* * * * *